US008563599B2

(12) United States Patent
Erhardt et al.

(10) Patent No.: US 8,563,599 B2
(45) Date of Patent: Oct. 22, 2013

(54) METHODS FOR SYNTHESIZING GLYCINOLS, GLYCEOLLINS I AND II, COMPOSITIONS OF SELECTED INTERMEDIATES, AND THERAPEUTIC USES THEREOF

(75) Inventors: Paul W. Erhardt, Toledo, OH (US); Rahul Khupse, Toledo, OH (US); Jefferey G. Sarver, Toledo, OH (US); Thomas E. Cleveland, New Orleans, LA (US); Stephen M. Boue, New Orleans, LA (US); Thomas E. Wiese, New Orleans, LA (US); Matthew E. Burow, New Orleans, LA (US); John A. McLachlan, New Orleans, LA (US)

(73) Assignees: The United States of America, represented by the Secretary of Agriculture, Washington, DC (US); Xavier University of Louisiana, New Orleans, LA (US); University of Toledo, Toledo, OH (US)

( * ) Notice: Subject to any disclaimer, the term of this patent is extended or adjusted under 35 U.S.C. 154(b) by 43 days.

(21) Appl. No.: 12/921,013

(22) PCT Filed: Mar. 3, 2009

(86) PCT No.: PCT/US2009/035803
§ 371 (c)(1),
(2), (4) Date: Dec. 15, 2010

(87) PCT Pub. No.: WO2009/111428
PCT Pub. Date: Sep. 11, 2009

(65) Prior Publication Data
US 2011/0144195 A1    Jun. 16, 2011

Related U.S. Application Data

(60) Provisional application No. 61/067,883, filed on Mar. 3, 2008.

(51) Int. Cl.
*A61K 31/352* (2006.01)

(52) U.S. Cl.
USPC ......................................................... 514/453

(58) Field of Classification Search
USPC ......................................................... 514/453
See application file for complete search history.

(56) References Cited

U.S. PATENT DOCUMENTS

2007/0037874 A1    2/2007  Yoo et al.

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Aardt, T.G. et al., "Synthesis of isoflavonoids. Enantiopure cis- and trans-6a-hydroxypteroxcarpans and a racemic trans-pterocarpan", Tetrahedron, 2001, 57, 7113-7126.
Khupse, R. et al., "Approaches toward the biomimetic total synthesis of the soybean flavoniods glyceollin I and II", In: 30th national medicinal Chemistry symposium. edited by by W. Nelson, University of Washington 2006, p. 84, See the abstract 87.
Dehury, S.K. et al., "Catalytic asymmetric dihydrioxylation of olefins with recyclable osmate-exchanged chloroapatite catalyst", Tetrahedron letters. 2007, 48, 2493=2496. ISSN: 0040-4039, See scheme 1, p. 2495 left col. lines 16-22.
Green, T.W. et al. "Protective Groups in Organic Synthesis" 3rd ed. Wiley-Interscience, 1999. ISBN: 0-471-16019-9, pp. 127-132.
Green, T.W. et al. "Protective Groups in Organic Synthesis" 3rd ed. Wiley-Interscience, 1999. ISBN: 0-471-16019-9, p. 257.
Aardt, T.G. et al., "Synthesis of isoflavonoids. Enantiopure cis- and trans-6a-hydroxypteroxcarpans and a racemic trans-pterocarpan", Tetrahedron, 2001, 57, 7113-7126. ISSN: 0040-4020.
Grotewold, Erich, "The Science of Flavonoids", Springer, 2006, ISBN-10: 0-387-28821-X, p. 30.
Kiss, L. et al., "Chiroptical properties and synthesis of Enantiopure cis and trans Ptercarpan Skeleton" Chirality. 2003, 15, 558-563, ISSN: 0899-0042.
International Search Report and Written Opinion of PCT/US2009/035803 dated Oct. 20, 2009 (16 pages).
Salvo et al. "Antiestrogenic Glyceollins Suppress Human Breast and Ovarian Carcinoma Tumorigenesis" Clin Cancer Research (2006); 12(23) pp. 7159-7164.

* cited by examiner

*Primary Examiner* — Kristin Vajda
(74) *Attorney, Agent, or Firm* — Miles & Stockbridge, P.C.

(57) ABSTRACT

Two distinct methods are disclosed and claimed for synthesizing glyceollin I plus glyceollin II as a mixture and as their pure forms. Stereochemical isomers and various synthetic intermediates are also synthesized and claimed for their novel compositions of matter. All compounds and their mixtures are claimed for use in formulations that are useful to treat or prevent cancer, or that have utility as selective estrogen receptor modulators, such formulations including enhanced or medical foods, dietary supplements and ethical pharmaceutical agents.

10 Claims, 16 Drawing Sheets

METHODS FOR SYNTHESIZING GLYCINOLS, GLYCEOLLINS I AND II, COMPOSITIONS OF SELECTED INTERMEDIATES, AND THERAPEUTIC USES THEREOF

CROSS-REFERENCE TO RELATED APPLICATIONS

This application is a §371 National Stage Application of PCT/2009/035803, which claims priority to U.S. Provisional Patent Application No. 61/067,883, filed on Mar. 3, 2008, and which is hereby incorporated by reference in its entirety.

STATEMENT REGARDING FEDERALLY SPONSORED RESEARCH OR DEVELOPMENT

The invention was made with U.S. Government support under grant number 512115 awarded by the United States Department of Agriculture. The United States Government has certain rights in the invention.

THE NAMES OF THE PARTIES TO A JOINT RESEARCH AGREEMENT

Not applicable.

INCORPORATION-BY-REFERENCE OF MATERIAL SUBMITTED ON COMPACT DISC

Not applicable.

BACKGROUND OF THE INVENTION

1. Field of the Invention

The present invention relates to: a) synthetic glyceollin I and glyceollin II, both as a mixture and as pure glyceollin I and pure glyceollin II; b) methods of synthesizing synthetic glyceollin I and glyceollin II; and c) methods of using synthetic glyceollin I and II.

2. Description of Related Art

The glyceollins (GLYs) are natural product compounds that display properties indicative for use as cancer prevention and treatment agents. See, e.g., N. T. Keen, J. L. Ingham, T. Hymowitz, J. J. Sims, S. Midland, *Biochem. System. Ecol.* 1989, 17, 395-398; V. Persky, L. Van Horn, *J. Nutr.* 1995, 125, 709S-712S; C. Herman et al., *J. Nutr.* 1995, 125, 757S-770S; B. M. Collins-Burow, M. E. Burow, B. N. Doung, J. A. McLachlan, *Nutr. Cancer* 2000, 38, 229-244; M. E. Burow et al., *J. Clin. Endrocrinol. Metab.* 2001, 86, 1750-1758; and V. A. Salvo et al., *Clin. Cancer Res.* 2006, 12, 7159-7164, each of which is hereby incorporated by reference in its entirety. To date, supplies of the GLYs must be obtained by their induced biosynthesis in soybean plant parts followed by tedious extraction and purification procedures which provide extremely low yields. See, e.g., T. Komives, *J. Chrom.* 1983, 261, 423-424; J. Huang, K. R. Barker, *Plant Physiol.* 1991, 96, 1302-1307; C. Kraus, G. Spiteller, A. Mithoefer, J. Ebel, *Phytochem.* 1995, 40, 739-743; R. Hammerschmidt, *Ann. Rev. Phytopath.* 1999, 96, 285-306; H. M. G. Al-Hazimi, H. Z. Alkhathlan, *J. King Saud Univ. Sci.* 2000, 12, 93-122; S. M. Boue, C. H. Carter, K. C. Ehrlich, T. E. Cleveland, *J. Agric. Food Chem.* 2000, 48, 2167-2172; J. Faghihi, X. Jiang, R. Vierling, S. Goldman, S. Sharfstein, J. Sarver, P. Erhardt, *J. Chrom. A* 2001, 915, 61-74; and T. E. Cleveland, S. M. Boue, M. E. Burow, J. A. McLachlan, U.S. Pat. Appl. Pub. No. 20060246162, each of which is hereby incorporated by reference in its entirety. Thus, there is an immediate need for improved methods to produce various GLY compounds for further development, as well as a longer-term need for producing large supplies of selected GLY members for eventual use within the marketplace. See, e.g., R. S. Khupse, P. W. Erhardt, 30*th National Medicinal Chemistry Symposium*, Seattle, June 2006, Poster #87; and R. S. Khupse, P. W. Erhardt, 234*th National ACS Meeting, Boston*, August 2007, Poster #MEDI-182, each of which is hereby incorporated by reference in its entirety. The present invention provides very practical methods for synthesizing GLYs I and II in higher yields than can be obtained by their extraction from induced soybean. In addition, these methods can be used to prepare a variety of GLY-related compounds, including glycinol and certain synthetic intermediates that have novel compositions of matter. The purified, individual GLY members, synthetic intermediates and selected analogs display useful pharmacological properties similar to the naturally-derived materials.

BRIEF SUMMARY OF THE INVENTION

In one aspect of this invention, two distinct methods are provided for preparing a mixture of GLY I plus GLY II, pure GLY I, pure GLY II, and several closely-related natural product family members. The first of these methods follows a biomimetic route. The second deploys a Wittig reaction as a key step. In a second aspect of the overall invention, these same methods are used to prepare the stereochemical racemates and non-natural enantiomers of the GLY I plus GLY II mixture, GLY I, GLY II, and several synthetic intermediates, all of which have novel compositions of matter. In a final aspect of this invention, selected compounds are shown to be useful in the prevention or treatment of certain cancers, while other selected compounds are shown to be useful as selective estrogen receptor modulators (SERMs) for the treatment of various menopausal-related conditions such as hot flashes.

One object of this invention is to allow the individually pure GLY compounds, synthetic intermediates or selected analogs, to be used in various single-component product formulations. A second object is to allow the single-components to be utilized as ingredients that can be added to enhance or fortify regular foods, medical foods or dietary supplement-related products. A third object is to allow for the production of a predetermined range of combined GLY-related compounds, wherein for the case of GLY I plus GLY II a ratio of about 5 to 1 can be achieved directly by synthesis, and wherein for all other cases, various ratios of various components can be achieved by selectively mixing the pure materials. These mixtures can be used in specific combination-component product formulations, or as specific combination-component ingredients that can be added to regular foods, medical foods or dietary supplement-related products. Additional objects and advantages of this invention will become apparent to those skilled in the art from the following descriptions and examples when read in light of the accompanying figures that convey specific chemical synthesis schemes and analytical data, and in light of the tabulated biological testing data. These descriptions are intended to generally encompass the cited references and their applicable organic synthesis or biological testing methodologies within the distinct context of the GLYs and the GLYs' immediately accessible synthetic intermediates.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements.

FIG. 7A shows natural (−) GLY I; FIG. 7B shows a racemic mixture of synthetic GLY I; FIG. 7C shows synthetic (−) GLY I; and FIG. 7D shows synthetic (+) GLY I.

FIG. 8A shows a racemic mixture of synthetic GLY I; FIG. 8B shows synthetic (−) GLY I spiked with natural (−) GLY I; and FIG. 8C shows synthetic (+) GLY I spiked with natural (−) GLY I.

DETAILED DESCRIPTION OF THE INVENTION

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Figure 1:
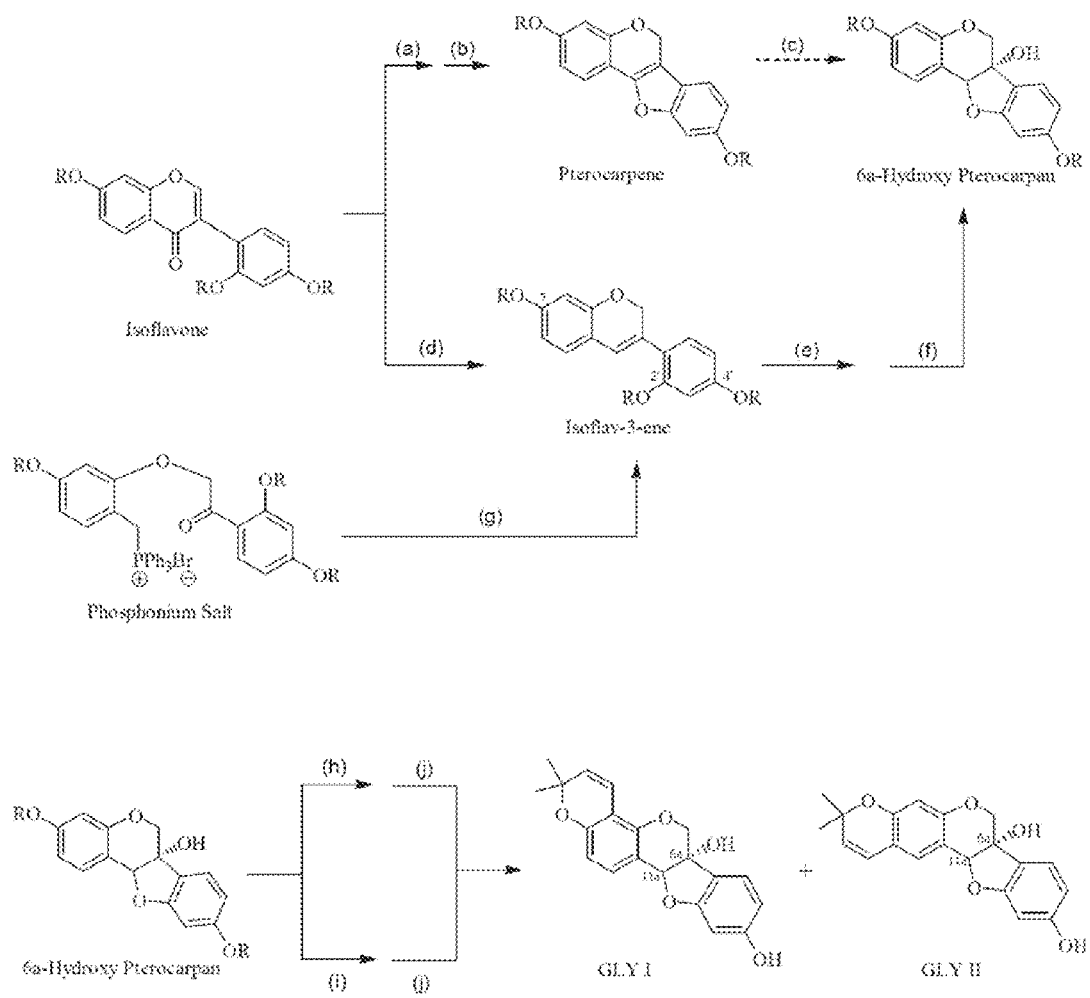
FIG. 1 (Scheme 1) is a general schematic illustration of the synthetic methods that were explored to prepare GLY I and GLY II via a biomimetic route that starts from an isoflavone and traverses either a pterocarpene or an isoflavene, and via a non-biomimetic route that utilizes an intermolecular Wittig reaction to produce the isoflavene from an appropriate ketone intermediate.

FIG. 1 shows Scheme 1, depicting general routes that were explored to prepare GLY I and II: (a) reduction; (b) ring closure; (c) hydration; (d) dehydration; (e) osmium tetroxide; (f) ring closure; (g) ylide reaction; (h) aldol condensation; (i) propargyl ether; and (j) deprotection. Depending upon the conditions of the chemical methods that are being deployed, the R group can independently be simple hydrogen or specific types of protecting groups that are compatible for use during a given series of synthetic steps. Referring to FIG. 1 (Scheme 1), GLYs I and II can be obtained from the 6a-hydroxypterocarpan intermediate by forming the isoprenyl-containing ring system via either route (h,j) or (i,j). The 6a-hydroxypetrocarpan, in turn, can be imagined to be prepared from either the pterocarpene (see R. S. Khupse, P. W. Erhardt, *J. Nat. Prod.* 2006, in press, which is incorporated by reference herein in its entirety) or the isoflav-3-ene. In particular, the inventors' experiments have indicated only the latter to be a practical route. In one inventive embodiment, the key isoflav-3-ene intermediate can be synthesized from an isoflavone by analogy to the biosynthesis of these types of materials within plants, hence the inventors' designation as a biomimetic route. See, e.g., R. Welle, H. Grisebach, *Arch. Biochem. Biophys.* 1988, 263, 191-198; and G. Kochs, H. Grisebach, *Arch. Biochem. Biophys.* 1989, 273, 543-553, each of which is hereby incorporated by reference in its entirety. In another inventive embodiment, the key isoflavene intermediate can be synthesized from its corresponding ylide via a novel Wittig reaction, and hence the inventors' designation as a non-biomimetic route. See, e.g., C. Burali, N. Desideri, M. L. Stein, C. Conti, N. Orsi, *Eur. J. Med. Chem.* 1987, 22, 119-123; and Y. Yuan, H. Men, C. Lee, *J. Am. Chem. Soc.* 2004, 126, 14720-14721, each of which is hereby incorporated by reference in its entirety.

Figure 2:
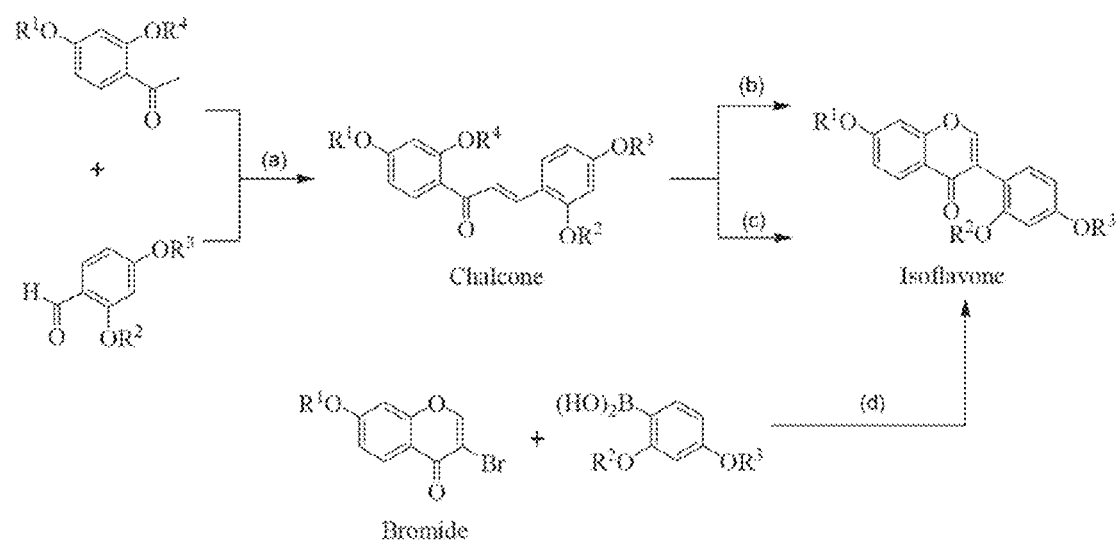
FIG. 2 (Scheme 2) is a general schematic illustration of the synthetic methods that were explored to produce the isoflavone via either a biomimetic route that traverses a chalcone, or a non-biomimetic route involving a Suzuki coupling reaction.

FIG. 2 shows Scheme 2, depicting overall routes to isoflavones: (a) Claisen-Schimidt condensation; (b) Koser's reagent; (c) thallium reagent; and (d) Suzuki coupling. Depending upon the conditions of the chemical methods that are being deployed, the $R^1$, $R^2$, $R^3$ and $R^4$ groups can independently be simple hydrogen or specific types of protecting groups that are compatible for use during a given series of synthetic steps. Referring to FIG. 2 (Scheme 2), the isoflavone used in the biomimetic route can be obtained by either a Koser's reagent (See, e.g., R. M. Moriarty, J. S. Khosrowshahi, O. Prakash, *Tet. Let.* 1985, 26, 2961-2964; and Y. Kawamura, M. Maruyama, T. Tokuoka, M. Tsukayama, *Synth.* 2002, 17, 2490-2496, each of which is hereby incorporated by reference in its entirety) or a thallium reagent (See, e.g., A. McKillop, B. P. Swann, E. C. Taylor, *J. Am. Chem. Soc.* 1973, 95, 3340-3343; A. McKillop, B. P. Swann, M. E. Ford, E. C. Taylor, *J. Am. Chem. Soc.* 1973, 95, 3641-3645; L. Farkas, A. Gottsegen, M. Nogradi, S. Antus, *Perkin Trans.* 1: *Org. Bio-Org. Chem.* 1974, 2, 305-312; E. C. Taylor, R. L. Robey, K. T. Liu, B. Favre, H. T. Bozimo, R. A. Conley, C. S. Chiang, A. McKillop, M. E. Ford, *J. Am. Chem. Soc.* 1976, 98, 3037-3038; M. Suesse, S. Johne, M. Hesse, *Helv. Chim. Acta* 1992, 75, 457-470; T. Horie, T. Yamada, Y. Kawamura, M. Tsukayama, M. Kuramoto, *J. Org. Chem.* 1992, 57, 1038-1042; and T. Horie, Y. Kawamura, C. Sakai, A. Akita, M. Sasagawa, T. Yamada, *Perkin Trans.* 1: *Org. Bio-Org. Chem.* 1996, 16, 1987-1992, each of which is hereby incorporated by reference in its entirety) mediated rearrangement and cyclization of the preceding chalcone. The chalcone, in turn, can be obtained by a well-behaved Claisen-Schmidt condensation.

See, e.g., F. C. Chen, T. S. Chen, T. Ueng, *J. Chinese Chem. Soc.* (*Taipei*) 1962, 9, 308-310; P. B. Anzeveno, *J. Org. Chem.* 1970, 44, 2578-2580; and M. Tsukayama, K. Fujimoto, T. Horie, M. Masumura, M. Nakayama, *Bull. Chem. Soc. Japan* 1985, 58, 136-141, each of which is hereby incorporated by reference in its entirety. Alternatively, the isoflavone can be derived via a Suzuki coupling strategy after preparation of the requisite bromide. See, e.g., Y. Hoshino, N. Miyaura, A. Suzuki, *Bull. Chem. Soc. Japan* 1988, 61, 3008-3010; and H. Chaumeil, S. Signorella, C. Le Drian, *Tetrahedron* 2000, 56, 9655-9662, each of which is hereby incorporated by reference in its entirety. Both the substitution pattern and choice of specific protecting groups ($R^1$ to $R^4$) influence the efficiency of these three routes. Given the distinct substitution pattern required for the GLYs, the inventors' experiments clearly established that the thallium-mediated route is the most practical when undertaken with the very select combination of protecting groups that are further described immediately below, and are also specifically disclosed within the subsequent detailed description of the biomimetic portion of the overall invention's preferred embodiments.

While a range of common protecting groups (R in Scheme 1; and $R^1$ to $R^4$ in Scheme 2) can be considered for deployment along various segments of the aforementioned routes, the inventors have discovered that it is most advantageous to use an electron withdrawing type of group for $R^4$ during conversion of the chalcones to isoflavones when following the biomimetic route shown in Scheme 2. For this same conversion, the inventors alternatively discovered that it is also advantageous to use non-electron withdrawing type of groups for $R^1$ and $R^2$. Finally, the inventors further discovered that it is most advantageous to use the same electron-withdrawing protecting group for both $R^1$ and $R^2$. In this way, these protecting groups can be removed later in a simultaneous fashion so as to allow for formation of a quinone-methide intermediate as a prelude to conducting the key central ring closure shown as step (f) in Scheme 1. It is the very reactive quinone-methide that ultimately becomes subject to attack by the simultaneously exposed hydroxyl ($R^2$=H) during this ring closure, all of which becomes a very distinct feature in the overall inventive method later depicted in the more detailed FIG. 5 (Scheme 5) steps (b) and (c).

Referring again to Scheme 2, the chalcone route to the isoflavone, step (a) plus step (b) or (c), is preferred to that utilizing a Suzuki coupling of the bromide depicted in step (d). Although the Claisen-Schmidt condensation, step (a), can be carried-out by deploying a variety of bases, in the instant case the use of piperidine in anhydrous methanol (see, e.g., P. B. Anzeveno, *J. Org. Chem.* 1970) is particularly advantageous because it avoids cyclization of the desired chalcone to an unwanted flavone (see, e.g., F. C. Chen, et al., *J. Chinese Chem. Soc.* (*Taipei*) 1962). Likewise, the rearrangement and cyclization process with thallium, step (c), is preferred to that which utilizes Koser's reagent, step (b). In terms of protecting groups, the particularly preferred and distinct inventive embodiment for the pathway (a) followed by (c) involves the use of $R^1$=$R^2$=Benzyl ("Bn"), $R^3$=Methoxymethyl ("MOM"), and $R^4$ while able to initially remain as the unprotected hydrogen ("H") for the first step (a), is advantageously converted to an acetyl group ("Ac") for the second step (c). The relatively small size and electron-withdrawing nature of the latter was found to be ideally suited for decreasing unwanted, alternative rearrangement possibilities that can also occur during formation of the isoflavone from the chalcone. See, e.g., A. McKillop, et al., *J. Am. Chem. Soc.* 1973, 95, 3340-3343; A. McKillop, et al., *J. Am. Chem. Soc.* 1973, 95, 3641-3645; E. C. Taylor, et al., *J. Am. Chem. Soc.* 1976; T. Hone, et al., *J. Org. Chem.* 1992; and T. Horie, et al., *Perkin Trans.* 1: *Org. Bio-Org. Chem.* 1996. Similarly, the MOM protecting group represents an ideal compromise of small size, stability under basic conditions, and facile cleavage under a specific range of acidic conditions. Finally, the use of a benzyl group for both $R^1$ and $R^2$ allows for their simultaneous removal just prior to later formation of the central dihydrobenzofuran ring system (later Scheme 5 and its associated discussion).

Figure 3:
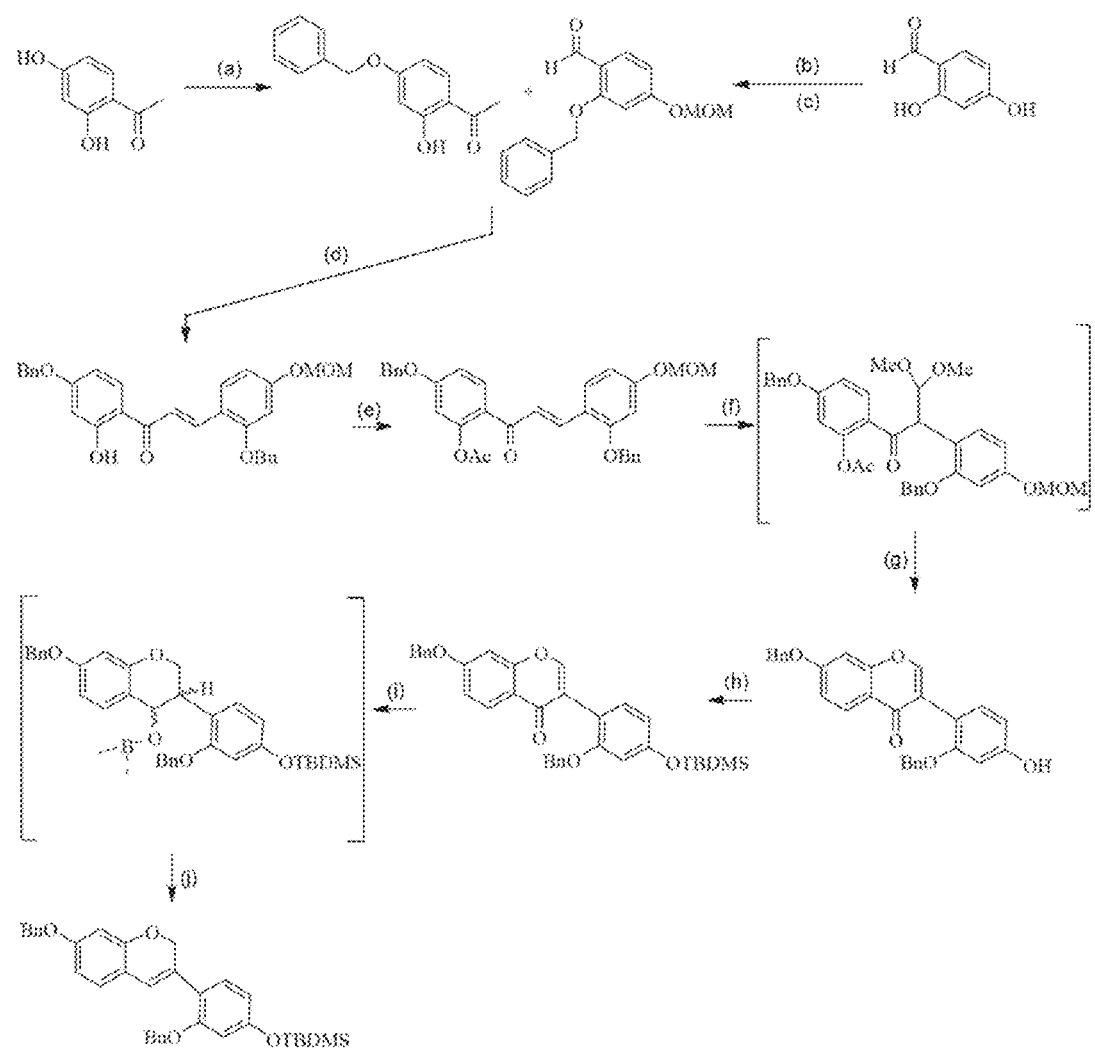
FIG. 3 (Scheme 3) is a schematic illustration of the specific synthetic method which represents the preferred embodiment used to prepare the key isoflavene intermediate by the biomimetic route.

When only methanol is used to form the intermediate acetal needed for the ring closure step (c) in Scheme 2, a complex mixture of products is obtained. Addition of trimethyl orthoformate ("TMOF") (see, e.g., E. C. Taylor, et al., *J. Am. Chem. Soc.* 1976) leads to a much cleaner reaction and a significantly improved yield. In the end, a 1:1 combination of methanol:TMOF represents a particularly preferred embodiment for this step of the overall inventive method. Acidic conditions are next deployed to form the isoflavone, wherein the acetyl is lost and successful ring closure is observed. In addition, when MOM is deployed as an initial protecting group, these conditions also remove the MOM group which is advantageous at this point because an even more labile protecting group conducive to later steps in the overall synthesis is desirable. In this regard, a tertiary-butyl-dimethyl-silyl ("TBDMS") (see, e.g., A. Kojima, T. Takemoto, M. Sodeoka, M. Shibasaki, *J. Org. Chem.* 1966, 61, 4876-4877, which is hereby incorporated by reference in its entirety) protecting group is a preferred embodiment to use either as an alternative at the start of the synthesis or via its specific incorporation at this point after the MOM group has been removed. TBDMS is stable to mild basic conditions and to hydrogenation, while being subject to eventual removal under neutral to weakly acidic conditions, all of which is beneficial during the later stages of these syntheses. This entire sequence of the distinctly preferred embodiments for this inventive portion of the overall synthesis is depicted in FIG. 3 (Scheme 3) which also conveys the complete biomimetic route to the key isoflav-3-ene. Percent yields for each step of FIG. 3 (Scheme 3) are given in parentheses immediately after the reaction conditions for each step (a) through (j): (a) BnBr, $K_2CO_3$, DMF, 88%; (b) MOMCl, $K_2CO_3$, Acetone; (c) BnBr, $K_2CO_3$, DMF, 74% combined yield across both (b) and (c); (d) Reflux, Piperidine, Anhy. MeOH, 84%; (e) Acetic anhydride, $NEt_3$, 92%; (f) $Tl(NO_3)_3$, MeOH:TMOF (1:1); (g) 10% Aq. HCl, 68% combined yield across both (f) and (g); (h) TBDMSCl, $NEt_3$, $CH_2Cl_2$, 90%; (i) $LiBH_4$, THF; (j) 10% Aq. HCl, 45% combined yield across both (i) and (j). Overall yield to produce isoflav-3-ene from commonly available commercial materials is 16%. In the last step, formation of the isoflav-3-ene can be accomplished by reduction of the isoflavone to an isoflavanol which is then prone toward spontaneous conversion to product upon treatment with aqueous acid such as HCl. See, e.g., A. Major, M. Nogradi, B. Vermes, M. Kajtar-Peredy, *Liebigs Ann. Chemie* 1988, 6, 555-558, which is hereby incorporated by reference in its entirety. The inventors found that reduction of the ketone to a hydroxyl occurs cleanly when excess lithium borohydride is used, and this smoothly undergoes 1,2-dehydration upon treatment with acid. However, the resulting chromene system is, itself, somewhat labile under these conditions, and it is thus critical to completely remove all traces of acid during the work-up. Yields for this step can vary with the higher-end being around 50%.

Figure 4:
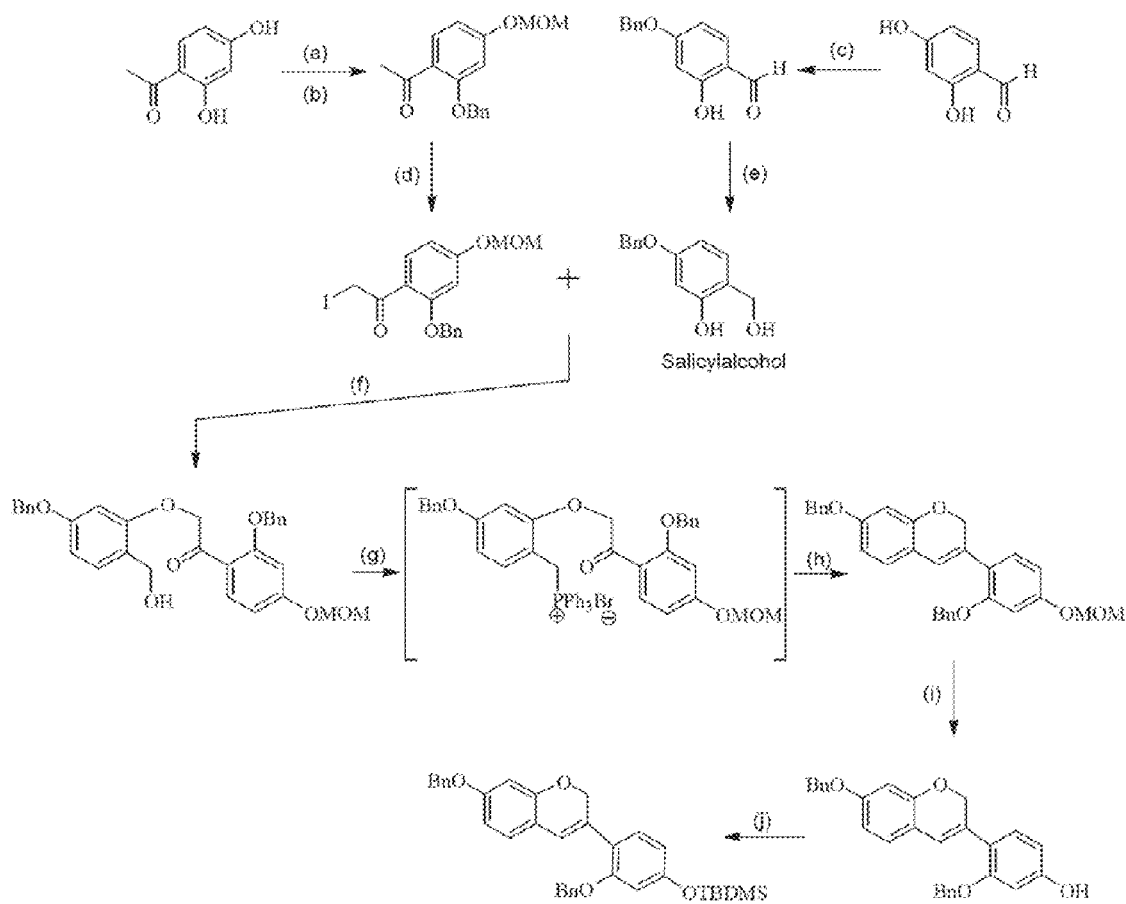
FIG. 4 (Scheme 4) is a schematic illustration of the specific synthetic method which represents the preferred embodiment used to prepare the key isoflavene intermediate by the non-biomimetic route.

The aforementioned biomimetic route is ideally suited for preparing GLY analogs related to the natural biosynthetic pathway. Alternatively, the other inventive embodiment involving the use of a novel Wittig reaction along a non-biomimetic route, is very useful for going directly to the isoflav-3-ene intermediate. Because this route does not entail the use of a thallium reagent, it represents a 'greener chemistry' pathway that can also be particularly beneficial for large-scale production processes. The non-biomimetic route is shown in FIG. 4 (Scheme 4) as its distinct and particularly preferred embodiments. The percent yields for each step of Scheme 4 are indicated immediately after the reaction condition: (a) MOMCl, $K_2CO_3$, Acetone; (b) BnBr, $K_2CO_3$, Acetone, combined yield across both (a) and (b) 71%; (c) BnBr, $NaHCO_3$, Acetonitrile, 80%; (d) $I_2$, Selectofluor™, MeOH, 70%; (e) $NaBH_4$, NaOH, Water:MeOH (1:1), 76%; (f) Reflux, $K_2CO_3$, Acetone, 72%; (g) $PPh_3$.HBr, Acetonitrile, RT; (h) Reflux, MeONa, MeOH, combined yield across both (g) and (h) 78% (i) Heat, $PPh_3$.HBr, Acetonitrile:Water; (j) TBDMSCl, $NEt_3$, $CH_2Cl_2$, combined yield across both (i) and (j) 69%. Overall yield to produce isoflav-3-ene from commonly available commercial materials is 19%. The first steps of this route involve parallel preparation of a salicylalcohol-related building block and an alpha-iodo-ketone building block. The inventors found the use of sodium bicarbonate in acetonitrile to be optimal for limiting benzylation (see, e.g., P. M. Dewick, *Syn. Comm.* 1981, 11, 853-857; and W. Y. Zhang, I. Lantos, R. T. Matsuoka, W. Mendelson, K. Webb, L. M. Tucker, L. Liu, G. Procter, PCT Int. Appl. 1996, 40 pp. WO 9619438 A1 1996027 Application: WO 95-US16975 19951222, each of which is hereby incorporated by reference in its entirety) to just the para-position of the aldehyde starting material for salicylalcohol. After observing decomposition under more standard conditions, the optimal way to subsequently reduce the aldehyde was found to be by using sodium borohydride in a solvent system specifically composed of 1:1 aqueous sodium hydroxide:methanol. See, e.g., M. Brink, *Acta Univ. Lund. Sect. II* 1965, 16, 1-11; W. Nagata, K. Okada, T. Aoki, *Synthesis* 1979, 5, 365-368; and M. L. Belyanin, V. D. Filimonov, E. A. Krasnov, *Russ. J. Applied Chem.* 2001, 74, 103-105, each of which is hereby incorporated by reference in its entirety. Furthermore, by evaporating the methanol prior to neutralization with 1 N sulfuric acid during this reaction's work-up, a very convenient isolation of the precipitated product can be achieved in 80% yield. Synthesis of the other building block begins with 2,4-dihydroxy-acetophenone, which is selectively protected with a silyl type of protecting group or by a MOM-group at the para-position, and by a benzyl-group at the ortho-position, followed by alpha-halogenation of the methylketone function. After observing a complex mixture of products using more conventional methods for bromination of the di-protected intermediate (see, e.g., L. C. King, G. K. Ostrum, *J. Org. Chem.* 1964, 29, 3459-3461; S. Cacchi, L. Caglioti, E. Cernia, *Synthesis* 1979, 1, 64-66; C. A. Horiuchi, S. Kiji, *Bul. Chem. Soc. Japan* 1997, 70, 421-426; and A. Fougerousse, E. Gonzalez, R. Brouillard, *J. Org. Chem.* 2000, 65, 583-586, each of which is hereby incorporated by reference in its entirety), the optimal way to halogenate this ketone was found to be by using 0.5 equivalents of iodine and 0.6 equivalents of Selectfluor™ (see, e.g., M. Jereb, S. Stavber, M. Zupan, *Synthesis* 2003, 6, 853-858, which is hereby incorporated by reference in its entirety) which provides the iodide in 70% yield after recrystallization from methanol:acetone.

Still referring to Scheme 4, the next step couples these two building blocks by using potassium carbonate in acetone. See, e.g., G. A. Kraus, I. Kim, *Org. Lett.* 2003, 5, 1191-1192, which is hereby incorporated by reference in its entirety. After completion of this reaction, the mixture can be poured into ice water to conveniently provide precipitated product in good yield (70%). This intermediate is now set for conducting an intramolecular Wittig reaction after initial formation of the phosphonium salt. When synthesis of the phosphonium salt was tried using triphenylphosphine hydrobromide in refluxing acetonitrile:water, a mixture of products was obtained due to the unanticipated deprotection of the MOM group. This reaction was subsequently accomplished without loss of the MOM-group by using freshly distilled acetonitrile at room temperature (see Y. Yuan, et al, *J. Am. Chem. Soc.* 2004), wherein a nearly quantitative yield was then obtained. Ring closure via the Wittig reaction is then well-behaved if sodium methoxide/methanol is used instead of n-butyl-lithium/THF, and wherein a 60% yield of recrystallized product can thus be obtained for the two-step process upon adopting both of these distinctly preferred embodiments.

If TBDMS is not already being utilized as a protecting group, at this point the inventors found it advantageous to again convert whatever other group (such as a MOM-protecting group) to a TBDMS group. As was planned in the biomimetic strategy, this allows for the protecting group's easy removal under neutral to weakly acidic conditions at the end of either of the overall synthetic routes. Clean removal of a MOM-protecting group at this juncture can be difficult even when several types of standard approaches are attempted. Alternatively, a preferred embodiment for this particular deprotecting step takes advantage of the conditions that had previously prompted the unanticipated loss of MOM, namely refluxing in acetonitrile:water with triphenylphosphine hydrobromide. This particular embodiment of the overall inventive methodology is an entirely new, novel, and very effective practical method to intentionally remove a MOM group within a general chemical context, as well as within the instant chemical compositions pertaining to production of the GLYs, and wherein the MOM can then be conveniently replaced by a TBDMS protecting group.

Figure 5:
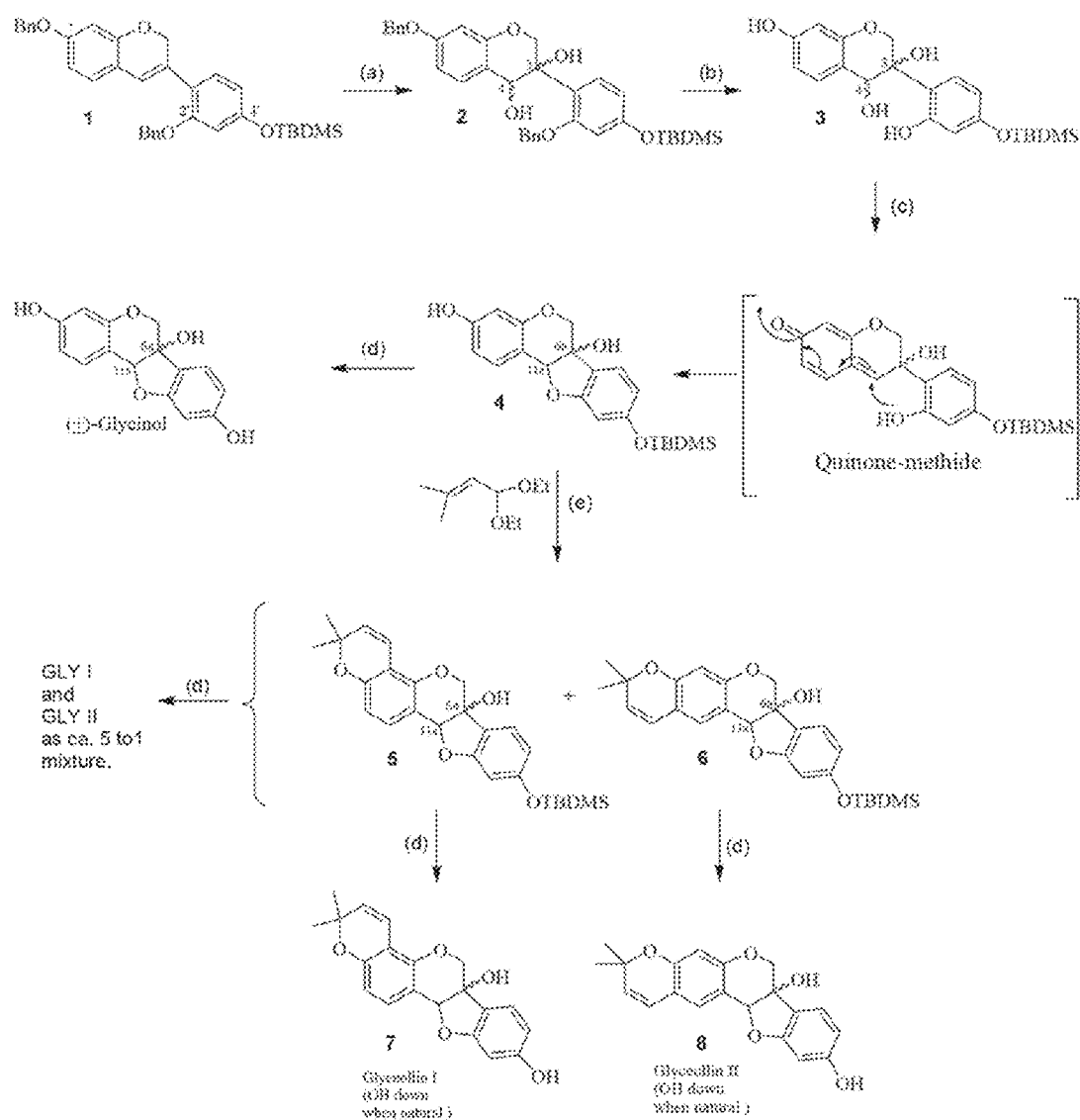
FIG. 5 (Scheme 5) is a schematic illustration of the specific synthetic methods which represent the preferred embodiments used to complete the syntheses of GLY I and GLY II, as their racemic mixtures and as their stereochemically pure enantiomers.

The remaining steps in the overall syntheses are common for both the biomimetic and non-biomimetic routes. These steps involve asymmetric dihydroxylation of the double-bond that was strategically placed within the isoflav-3-en, followed by cis-ring closure and elaboration of the final, isoprenyl-containing ring systems. The preferred embodiments for this chemistry are shown in FIG. 5 (Scheme 5). Pinard et al. (E. Pinard, M. Gaudry, F. Henot, A. Thellend, *Tet. Lett.* 1998, 39, 2739-2742, which is hereby incorporated by reference in its entirety), and more recently Aardt et al. (T. G. van Aardt, H. van Resnburg, D. Ferreira, *Tetrahedron* 2001, 57, 7113-7126, which is hereby incorporated by reference in its entirety), have reported upon the utility of the dihydroxylation approach within articles pertaining to other 6a-hydroxypterocarpans. The percent yields for each step of Scheme 5 are indicated immediately after the reaction condition: (a) [Non-asymmetric] $OsO_4$, NMO, Methylsulfonamide, Acetone, RT, 90%; [Asymmetric for natural] $OsO_2$; $(DHQD)_2PHAL$, $CH_2Cl_2$, −78° C., 70%; [Asymmetric for unnatural] $OsO_4$, $(DHQ)_2PHAL$, $CH_2Cl_2$, −78° C., 66%; (b) $H_2$, Pd—C (10%), Acetone, 89%; (c) Reflux, Base, Anhy. Ethanol, 60%; (d) $NEt_3$.3HF, Acetonitrile, 65%; (e) Heat, Xylene, Picoline, 60%. The squiggle bond represents either the racemic mixture, the pure natural enantiomer or the pure non-natural enantiomer, all of which can be obtained depending upon which catalyst is deployed in step (a). The average overall yields for all stereochemical forms are: GLY I 16%, GLY II 3%, Glycinol 30%. Because the central dihydrobenzopyran is now in-place, formation of the dihydrobenzofuran ring results exclusively in a 6a,11a-cis-arrangement. See, e.g., F. C. Chen, et al., *J. Chinese Chem. Soc. (Taipei)* 1962; and T. G. van Aardt, et al., *Tetrahedron* 2001. As a consequence, the inventors discerned that it becomes possible to completely control the stereochemistry of both steps by deploying a chiral additive during an osmium tetroxide (OT) dihydroxylation reaction. In this regard, various cinchona alkaloid derivatives have been used extensively as chiral ligands for asymmetric dihydroxylation. In addition, the choice for which type to deploy can be ascertained by using the Sharpless mnemonic model. See, e.g., P. Norrby, C. Hartmuth, K. B. Sharpless, *J. Am. Chem. Soc.* 1994, 116, 8470-8478, which is hereby incorporated by reference in its entirety. The inventors' analysis indicated that addition of (DHQD)2-PHAL as the chiral ligand should cause the two oxygen atoms to be delivered in a manner that produces the diol (compound 2 in Scheme 5 wherein both of the OH groups are pointed down) needed for eventual production of the natural form of the GLYs. This was then confirmed via the inventors' experiments as later discussed below.

Previous studies have shown that stoichiometric amounts of OT are typically required during these types of dihydroxylation reactions because the OT forms a stable osmate ester during the course of the reaction that precludes recycling of the osmium. See, e.g., E. Pinard, et al., *Tet. Lett.* 1998. Nevertheless, with a goal of conducting greener chemistry that might be useful for larger scale-up, the inventors first explored the possibility of reducing the OT load in a non-asymmetric fashion (i.e. without using a chiral additive) by examining the addition of a secondary oxidant, as well as by surveying different solvents and reaction temperatures and durations. When one equivalent of methanesulfonamide is used, breaking of the osmate ester is facilitated and this allows for recycling of osmium. See, e.g., H. C. Kolb, M. S. van Nieuwenhze, K. B. Sharpless, *Chem. Rev.* 1994, 94, 2483-2547, which is hereby incorporated by reference in its entirety. In the end, N-methylmorpholine oxide (NMO) proved to be the most efficient secondary oxidant, and acetone:water proved to be the best solvent media in terms of various reactant solubilities. Remarkably, this combination of methanesulfonamide and NMO enables the transformation to take place in high yield (90%) while using only 10 mg of OT for 10 mmole of reactant compared to the stoichiometric amount which would have required 2.5 g of OT. Thus, the highly preferred embodiment for this particular step of the overall synthetic process when directed toward the synthesis of racemic versions of the GLYs, is exactly as specified above. Alternatively, when the (DHQD)2-PHAL reagent was next added to this procedure as a chiral ligand, the anticipated enantioselectivity was not observed and the inventors' uniquely modified process was found to still produce a nearly racemic mixture. In order to obtain the pure enantiomers of GLY I and II, stoichiometric amounts of both OT and the chiral ligand must be deployed. At this point of the overall synthesis, this is optimally accomplished in methylene chloride as solvent at −78° C. Therefore, these latter conditions represent the preferred embodiments for obtaining the pure enantiomeric forms of GLY I and II, including their natural isomers which, after completing the remaining synthetic steps in Scheme 5, are thus afforded as only one enantiomer in high enantiomeric excess (ee). Enantiomeric purity or "ee" can be assessed at this intermediate stage by undertaking nuclear magnetic resonance (NMR) spectroscopy studies with chiral shift reagent additives, and by undertaking circular dichroism (CD) studies. In the NMR, the protons at positions at C-4 and C-8 are especially characteristic for stereochemical orientation and are useful diagnostics. Similarly, the CD studies can take advantage of results reported for the related diol prepared by Mori and Kisida, (see, e.g., K. Mori, H. Kisida, *Liebigs Ann. Chemie* 1989, 1, 35-39, which is hereby incorporated by reference in its entirety) namely (−)-pisatin which shows a strong negative Cotton effect at 233 nm and a moderately positive Cotton effect at 297 nm.

Still referring to Scheme 5, the next step (b) involves debenzylation of diol 2 to the tetrol 3 with the likelihood for spontaneous cyclization to the protected glycinol 4 via a quinone-methide type of reactive intermediate. Prasad et al. (A. V. K. Prasad, R. S. Kapil, S. P. Popli, P. Satya, *Perkin Trans.* 1: *Org. Bio-Org. Chem.* 1986, 9, 1561-1563, which is hereby incorporated by reference in its entirety) introduced this 'one-pot' method for reductive cyclization, and it was later used successfully by Pinard et al. (E. Pinard, et al., *Tet. Lett.* 1998) during their synthesis of pisatin. However, when this one-pot process was attempted on racemic material, there was no evidence for cyclized product immediately after filtering and evaporating the reaction medium prior to any significant work-up (crude product analysis by NMR). This difference may be due to the work-up that Pinard et al. deployed wherein pyridine was added after removal of the benzyl groups so as to avoid acid catalyzed loss of the 6a-hydroxyl-group from the cyclized product. Using their exact work-up procedure, the inventors observed only small amounts of cyclized product for the case of the inventors' instant molecular arrangements that will eventually lead to GLY I and GLY II. Furthermore, attempts to drive this dual process to higher completion by adding more pyridine or prolonging the heating, resulted in formation of black polymeric material, testifying to the reactivity of the inventors' particular quinone-methide when present as a concentrated solution. Because the inventors unexpectedly found that the inventors' particular tetrol is, itself, stable, the inventors instead determined that it is highly advantageous to first isolate 3 and then perform the cyclization as a separate step, rather than to use a 'one-pot' method that would otherwise seem to be advantageous. In addition, to allow for the intramolecular ring closure reaction while discouraging polymerization, the inventors found that it is preferable to use a dilute solution rather than a concentrated solution. Finally, because water is formed as a by-product, the inventors found that the addition of molecular sieves can assist in driving the cyclization forward. In the end, polymer-bound 1,3,4,6,7,8-hexahydro-2H-pyrimido[1,2-a]pyrimidine (see, e.g., W. Xu, R. Mohan, M. M. Morrissey, *Tet. Lett.* 1997, 38, 7337-7340, which is hereby incorporated by reference in its entirety) was deployed as a base in anhydrous ethanol over molecular sieves, and a remarkable 50% overall yield across these two steps was achieved. The resulting glycinol shown as its racemate and still protected with TBDMS (compound 4 in Scheme 5) can either be de-blocked to provide the racemic, unnatural analog or natural form of this natural product depending upon the stereochemistry of the dihydroxylation step (a), or carried forward through the remainder of the synthetic steps shown in Scheme 5. For example, the inventors' same, two-step chemical process is preferably utilized on the pure enantiomer forms of the terol 3 to also provide the natural (−)- and the unnatural (+)-glycinol-TBDMS intermediates in about 55% overall yields, the pure enantiomers being needed for eventual conversion to the natural and unnatural GLY I and GLY II products. The absolute stereochemistry and enantiomeric purity of these materials can again be confirmed by using NMR and CD. According to the literature (see, e.g., T. G. van Aardt, et al., *Tetrahedron* 2001), the NMR shift of the C-11a proton is diagnostic for defining a cis versus a trans ring closure within these types of systems. In this regard, the C-11 signal is at about 5.2 ppm which is in perfect accord with those of the cis isomers for variabilin and for pisatin as reported by Aardt et al. and by Mori et al., respectively. See, e.g., T. G. van Aardt, et al., *Tetrahedron* 2001; and K. Mori, et al., *Liebigs Ann.*

*Chemie* 1989. The assignment of absolute configuration for other 6a-hydroxypterocarpan structures and the Cotton effects observed in their CD spectra have been summarized by Slade et al. (D. Slade, D. Ferreira, J. P. J. Marais, *Phytochem.* 2005, 66, 2177-2215, which is hereby incorporated by reference in its entirety). Characteristically, the natural (−)-(6aS,11aS) cis isomers have a strongly negative Cotton effect between 220-250 nm with a weaker positive effect between 270-300 nm (and vice versa for the unnatural (+) cis isomers), whereas the unnatural trans enantiomers have either a weaker and stronger negative effect, or a weaker and stronger positive effect at these same wavelengths. In the instant case, the CD spectra for the (−)-glycinol-TBDMS compound was also found to match perfectly with the CD spectra obtained for the natural (−)-cis isomer.

Formation of the final ring system can be accomplished by either of two approaches for the assembly of isoprenyl(3,3-dimethylallyl) containing chromene systems, namely that of a modified aldol condensation (see, e.g., J. T. North, D. R. Kronenthal, A. J. Pullockaran, S. D. Real, H. Y. Chen, *J. Org. Chem.* 1995, 60, 3397-3400, which is hereby incorporated by reference in its entirety) or that of a Harfenist-Thom rearrangement of the propargyl ether of phenol. See, e.g., M. Harfenist, E. Thom, *J. Org. Chem.* 1972, 37, 841-848; and D. G. Clarke, L. Crombie, D. A. Whiting, *Perkin Trans.* 1: *Org. Bio-Org. Chem.* 1974, 9, 1007-1015, each of which is hereby incorporated by reference in its entirety. In either strategy, GLY I can be expected to be the major product and GLY II a secondary product. Thus, this methodology can afford both GLY I and GLY II from the same reaction. Both approaches were examined in parallel while initially using racemic material. Introduction of a dimethylpropargyl group proved to be very tedious, and depending upon various basic conditions, appeared to readily cause collapse of the glyceollin skeleton. Alternatively, the aldol approach shown as step (e) in Scheme 5 proved to be very useful. This approach is preferably undertaken by condensation of the keto-form of the phenol with an unsaturated aldehyde, the latter masked as its acetal to prevent self-polymerization, by refluxing in pyridine and with continuous removal of the alcohol liberated from the acetal. It is applicable only for cases where the phenol can undergo tautomerization to its phenone. In the end, the inventors found that the optimal conditions for this condensation became refluxing the starting material with the isoprenyl synthon in p-xylene using 0.25 equivalents of picoline as base. The TBDMS-protected forms of both GLY I and GLY II are obtained (compounds 5 and 6, respectively), with the more abundant being the GLY I regioisomer when assessed at the crude product stage by NMR. Separation of GLY I-TBDMS from GLY II-TBDMS was readily accomplished as part of the workup of the reaction by using silica column chromatography with dichloromethane as eluent to afford a 50% yield of TBDMS-GLY I and a 10% yield of TBDMS-GLY II. This same chemistry was also performed with the pure enantiomer starting materials and proceeds similarly, although (−) GLY-I-TBDMS is then obtained in an even somewhat higher yield (61%).

To complete the syntheses, de-protection with basic reagents like silica-supported TBAF or TAS-F (see, e.g., A. Gambacorta, S. Turchetta, M. Botta, *Synth. Comm.* 1989, 19, 2441-2448; and A. G. M. Barrett, M. Pena, J. A. Willardsen, *J. Org. Chem.* 1996, 61, 1082-1100, each of which is hereby incorporated by reference in its entirety) were tried, but these resulted in significant degradation of the formed products. After isolating small quantities of racemic GLY I and conducting a stability study by using HPLC, the inventors discovered that this ring system is not stable in basic pH above 8 while having reasonable stability down to an acidic pH as low as 4. This instability could derive by formation of a quinone-methide from the now unprotected 'Southern' ring's phenolic hydroxyl-group. Thus, mildly acidic reagents that might be used for de-protection were explored. In the end, $NEt_3.3$ HF (see, e.g., L. D. Julian, J. S. Newcom, W. R. Roush, *J. Am. Chem. Soc.* 2005, 127, 6186-6187, which is hereby incorporated by reference in its entirety), which provides a pH in the range of 4-5 when run on the 0.1 mmole scale in anhydrous acetonitrile, was most successfully utilized for this transformation. Even with this approach, however, it is important to adjust the pH of the post-reaction medium (as readily followed by TLC) to pH 7-8 by addition of triethylamine so as to avoid decomposition during subsequent workup. Final compounds are obtained in the range of ca. 65-70% yields. Assignment of stereochemistry for these final materials can be accomplished with NMR and CD. In addition, at this point it is convenient to take advantage of chiral HPLC wherein authentic materials from natural sources can be used as standards along with the synthesized racemic materials.

Figure 6A:
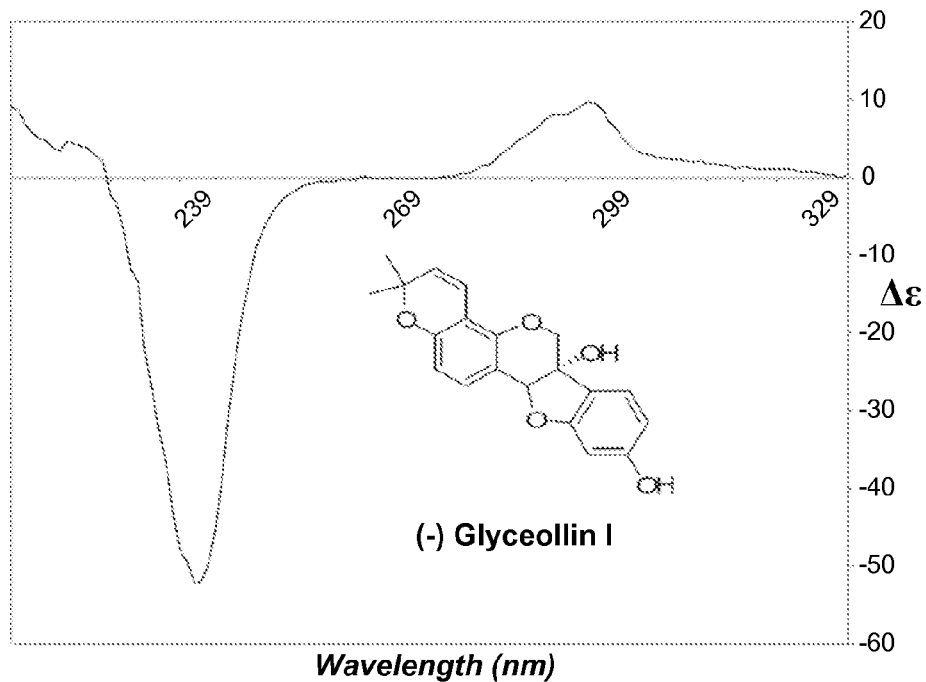
FIGS. 6A and 6B depict the Circular Dichroism (CD) spectra for both (−)-GLY I natural form (FIG. 6A) and (+)-GLY I unnatural form (FIG. 6B).
Figure 6B:
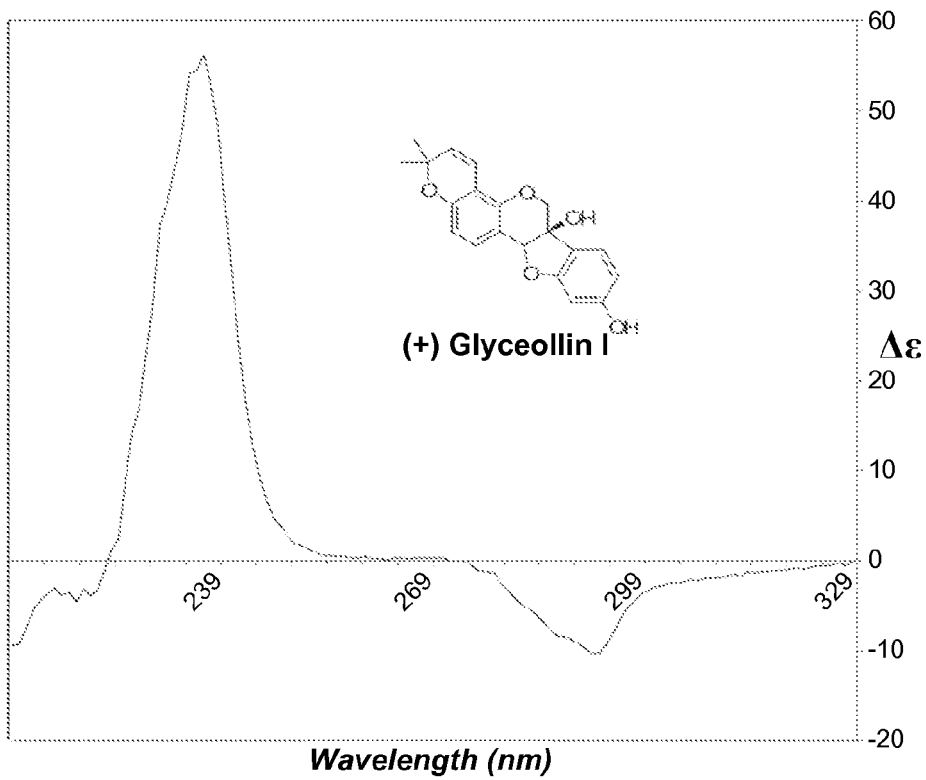
Figure 7A:
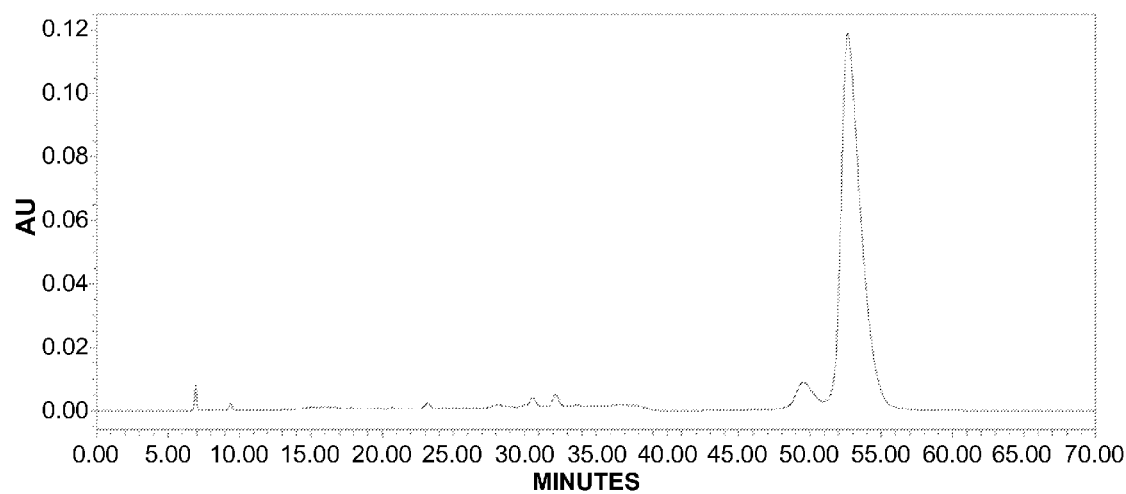
FIGS. 7A, 7B, 7C, and 7D depict chiral High-Performance Liquid Chromatography (HPLC) spectra for the racemic (±) and enantiomeric forms of GLY I.
Figure 7B:
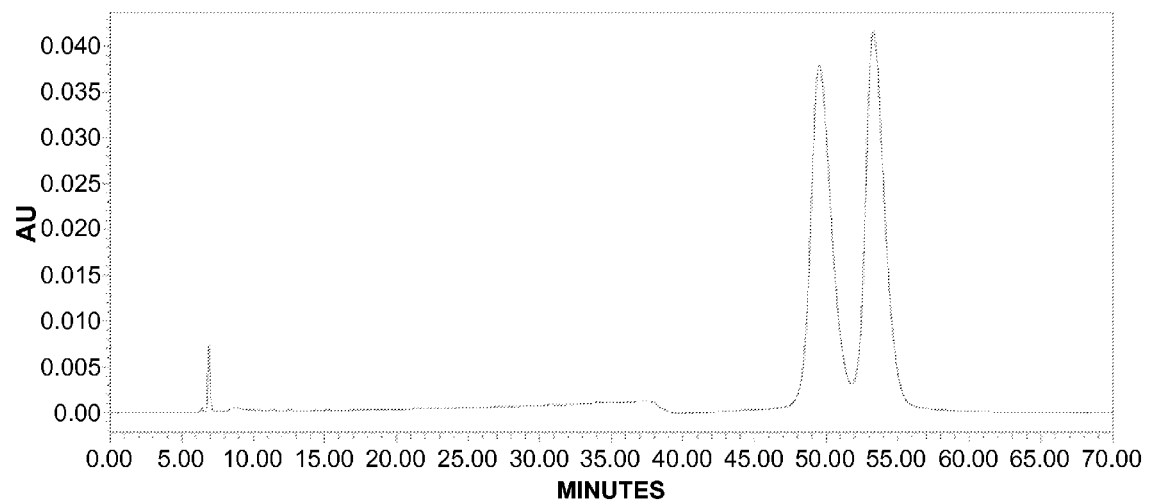
Figure 7C:
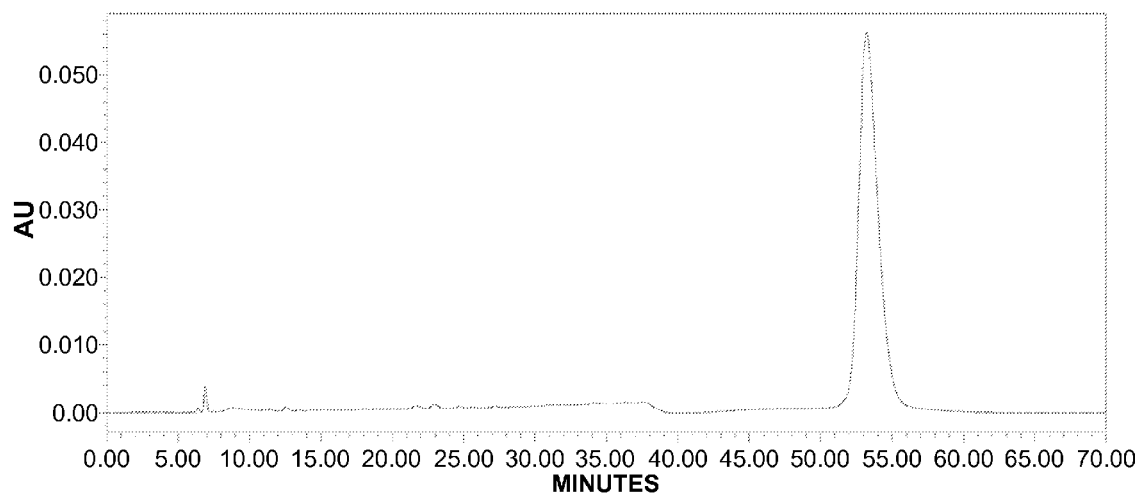
Figure 7D:
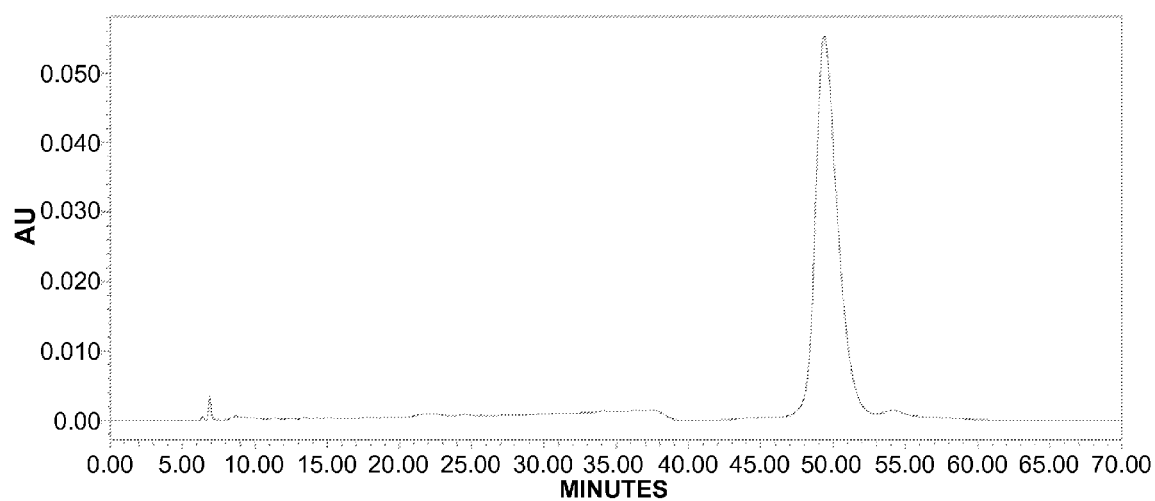
Figure 8A:
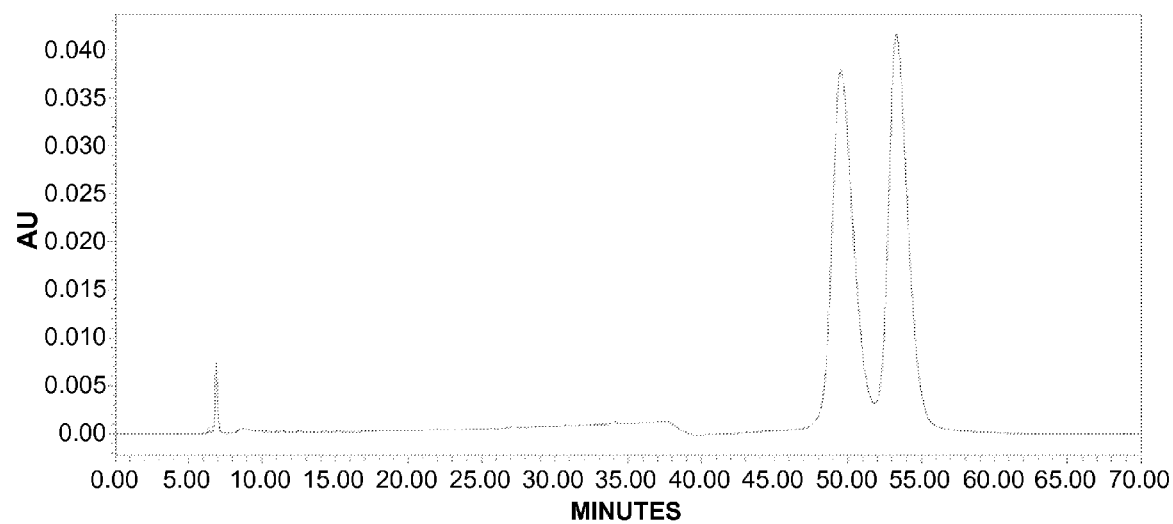
FIGS. 8A, 8B, and 8C depict chiral High-Performance Liquid Chromatography (HPLC) spectra for chromatographic spiking experiments deploying natural product standards.
Figure 8B:
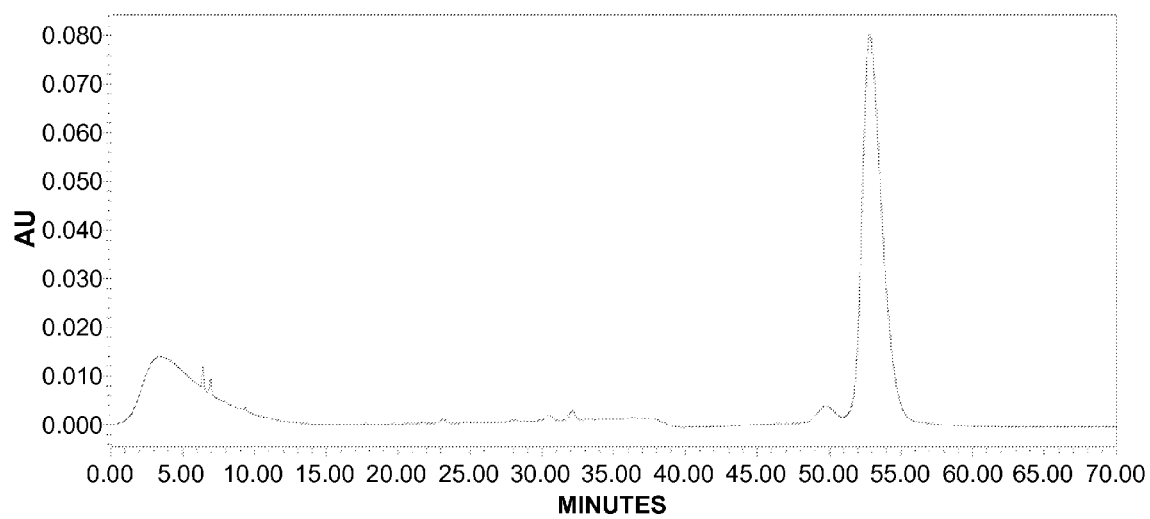
Figure 8C:
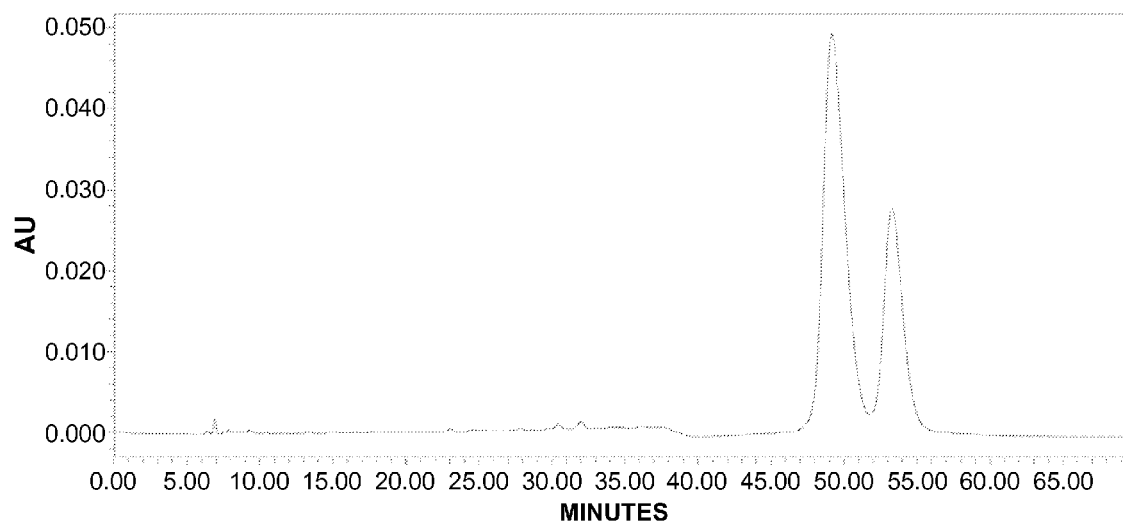

The proton NMR spectra of the synthesized GLYs closely match the data provided by Lyne et al. for the natural materials isolated from soy, all of which bear cis (6aS,11aS) stereochemistry. See, e.g., R. L. Lyne, L. J. Mulheirn, D. P. Leworthy, *Chem. Comm.* 1976, 13, 497-498, which is hereby incorporated by reference in its entirety. Most conspicuous are the protons at C-6 which appear as two separate doublets with the C-6 equatorial proton downfield compared to the C-6 axial proton, and wherein W coupling occurs with the C-11a proton, an event not possible for the trans system. Both COSY and NOSEY spectra also can be used to confirm this relationship between the C-6 equatorial and C-11a protons. Absolute stereochemistry can be confirmed by CD and chiral HPLC studies. As before, the CD spectra for the pure enantiomers (exemplary data for synthetic (−) GLY I and (+) GLY I is shown in FIGS. 6A and 6B, respectively) exhibit a strongly negative Cotton effect in the range 225-255 nm ($\pi,\pi^*$) and a weaker positive Cotton effect in the range 275-305 nm ($\pi,\pi^*$). Cyclodextrin-based Cylcobond™ chiral columns have been used by others to separate various chiral isochromene and dihydrobenzofuran derivatives. Since the GLYs contain both of these structural motifs, an HPLC method was developed using this column. A gradient elution with water:methanol:acetonitrile provided a baseline separation of the enantiomers within the GLY I racemic mixture which displayed two equal area peaks having retention times of 49 and 53 minutes. Application of authentic natural (−) GLY I yielded a major peak having a retention time of 53 minutes, as did the single peak observed for the synthesized pure enantiomer. Exemplary HPLC studies with specific results for naturally isolated GLY I, and for synthesized racemic, natural (−) and unnatural (+) GLY I are shown in FIGS. 7A, 7B, 7C, and 7D, respectively. Exemplary HPLC studies with specific results for chromatographic spiking experiments deploying natural product standards are shown in FIGS. 8A, 8B, and 8C. FIG. 8A shows a racemic mixture of synthetic GLY I; FIG. 8B shows synthetic (−) GLY I spiked with natural (−) GLY I; and FIG. 8C shows synthetic (+) GLY I spiked with natural (−) GLY I. For FIGS. 7A-7D and 8A-8C, Cyclobond™ columns were used, and the solvent system was water:methanol:acetonitrile (50:40:10).

While the natural product GLY mixtures obtained from stressed soybean plant parts have previously been reported to have interesting biological properties (see, e.g., N. T. Keen, et al., *Biochem. System. Ecol.* 1989; V. Persky, et al., *J. Nutr.* 1995; C. Herman et al., *J. Nutr.* 1995; B. M. Collins-Burow, et al., *Nutr. Cancer* 2000; M. E. Burow et al., *J. Clin. Endro-* crinol. Metab. 2001; V. A. Salvo et al., *Clin. Cancer Res.* 2006; T. Komives, *J. Chrom.* 1983; J. Huang, et al., *Plant Physiol.* 1991; C. Kraus, et al., *Phytochem.* 1995; R. Hammerschmidt, *Ann. Rev. Phytopath.* 1999; H. M. G. Al-Hazimi, et al., *J. King Saud Univ. Sci.* 2000; S. M. Boue, et al., *J. Agric. Food Chem.* 2000; J. Faghihi, et al., *J. Chrom. A* 2001; T. E. Cleveland, et al., U.S. Pat. Appl. Pub. No. 20060246162; R. S. Khupse, et al., 30*th National Medicinal Chemistry Symposium, Seattle, June* 2006; R. S. Khupse, et al., 234*th National ACS Meeting, Boston, August* 2007), the inventors discovered and disclose herein that certain of the individually purified GLY materials, synthetic intermediates and closely related natural product family members also display very promising novel activities indicative for use as cancer preventative and cancer treatment agents, as well as certain other clinical indications such as selective estrogen receptor modulators or SERMs. Representative results are summarized below for selected biochemical, cell culture and in vivo studies. The specific details associated with the experiments used to obtain these results are provided within the next 'Examples' section.

It can be expected that the antioxidant activities for the synthesized and stereoisomeric versions of the GLY I and GLY II compounds will be essentially identical to those for the natural GLY materials. Similarly, it follows that the synthetic intermediates having additional phenolic hydroxyl-groups such as glycinol or the 'tetrol' intermediate, should demonstrate somewhat higher antioxidant properties, and particularly so when these additional functionalities are unmasked from their respective protecting groups. This general trend was observed when various compounds were tested. The results from several selected compounds studied in the inventors' antioxidant assay are provided in the following Table 1. Daidzein and genistein were used as standards. Most of the compounds exhibit about ⅔ of the antioxidant activity of these standards. Glycinol is about equiactive to the standards. The weak activity observed for racemic 2 (compounds are numbered according to Scheme 5) is probably due to the loss of the 3,4-double bond which otherwise allows the oxygen atoms present as substituents on both of the aromatic rings in the synthesized compounds, to be in a chemical dialogue that is conducive to antioxidant activity.

TABLE 1

| | ABTS Antioxidant Assays | | |
|---|---|---|---|
| Agent ID | n | IC$_{50}$ (µM) | Trolox Equivalents (µmol/µmol) |
| Daidzein | 3 | 3.3 ± 0.2 | 3.0 ± 0.1 |
| Genistein | 3 | 3.3 ± 0.1 | 3.0 ± 0.1 |
| 4 (−) | 3 | 5.0 ± 0.5 | 1.9 ± 0.1 |
| 4 (+) | 3 | 5.0 ± 0.4 | 1.9 ± 0.1 |
| 4 (+/−) | 3 | 4.6 ± 0.2 | 2.0 ± 0.1 |
| 7 (+) | 3 | 5.2 ± 0.3 | 1.8 ± 0.1 |
| 7 (−) | 3 | 5.3 ± 0.3 | 1.8 ± 0.1 |
| Glycinol (+/−) | 4 | 3.5 ± 0.3 | 2.8 ± 0.2 |
| 2 (+/−) | 3 | >>100 | 0.008 ± 0.006 |
| 3 (+/−) | 3 | 4.6 ± 0.3 | 2.0 ± 0.1 |

"Agent ID" numbers refer to those specified in FIG. 5 (Scheme 5). Racemates are designated as (+/−) and enantiomers by either (−) or (+). Experimental details are provided in the Examples section.

Figure 9:
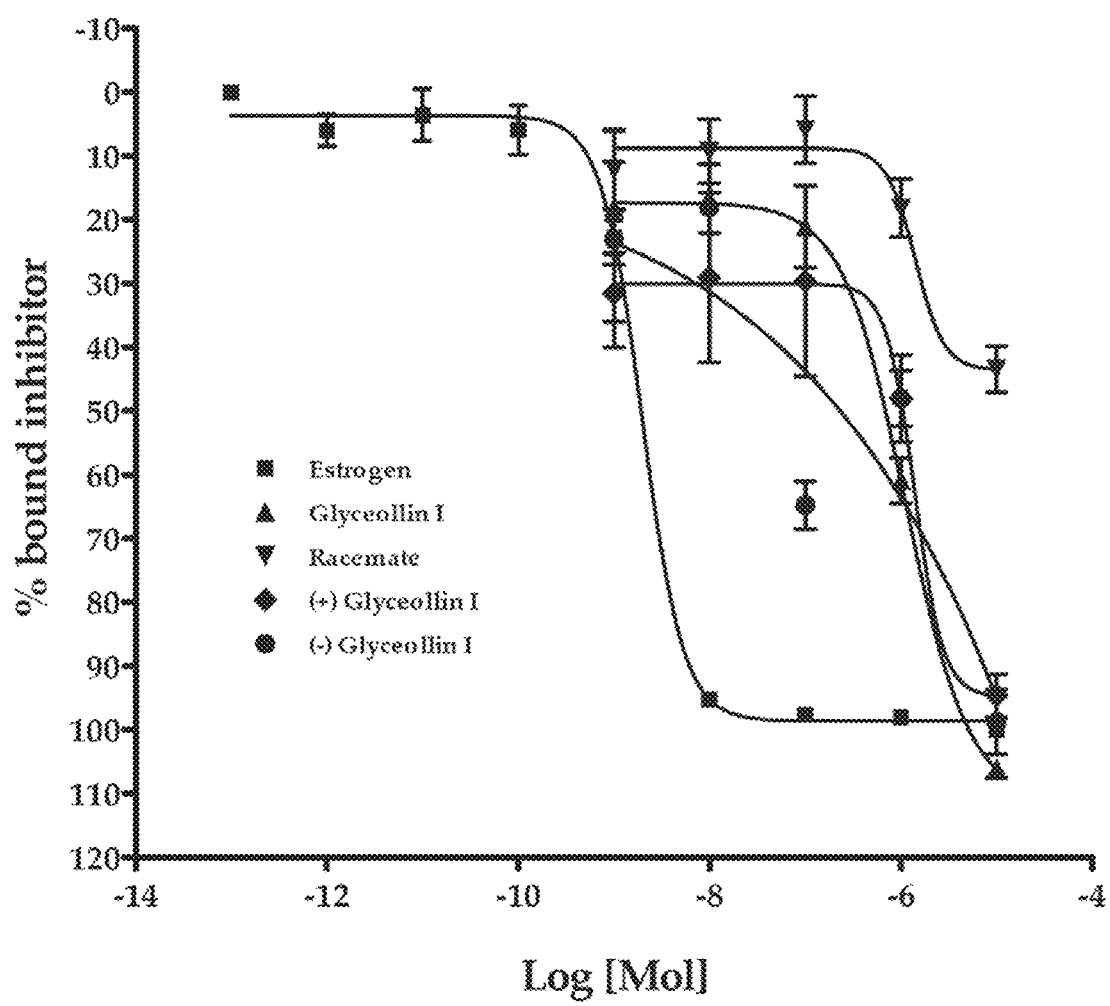
FIG. 9 shows the interaction of representative compounds with alpha-estrogen receptors (ERα) using natural estrogen as the standard for 100% binding.

Because the interaction of the GLYs with the estrogen receptors will involve associations between very specific molecular features in a three-dimensional manner, it is not to be expected that the racemic, natural and unnatural stereoisomers will necessarily demonstrate similar activity. As a general observation, the inventors found that the IC50 values calculated for 50% inhibition of a standard's binding with the alpha estrogen receptor (ER-α) were 1.4 µM for the synthesized natural (−)-GLY I, unnatural (+)-GLY I, and racemic (±)-GLY I, all of which compare rather closely to the IC50 value of 1.1 µM obtained for GLY I isolated from natural soy sources. This data is shown in FIG. 9 wherein it can also be seen that all of these compounds bind with the estrogen receptor about 100 to 1,000 fold less strongly than estrogen itself. FIG. 9 shows competition binding curves of isolated GLY I, synthetic racemic (±)-GLY I, synthetic unnatural (+)-GLY I, and synthetic natural (−)-GLY I to ERα. Increasing concentrations of isolated GLY I, racemate, (+) and (−) isomers were added to ERα/ES2 complex and compared with E2. Data points and error bars represent the mean±SEM of three experiments for isolated GLY I, racemate, (+) and (−) isomers and ten experiments for E2 treatment for each concentration tested. (p<0.05)

Figure 10:
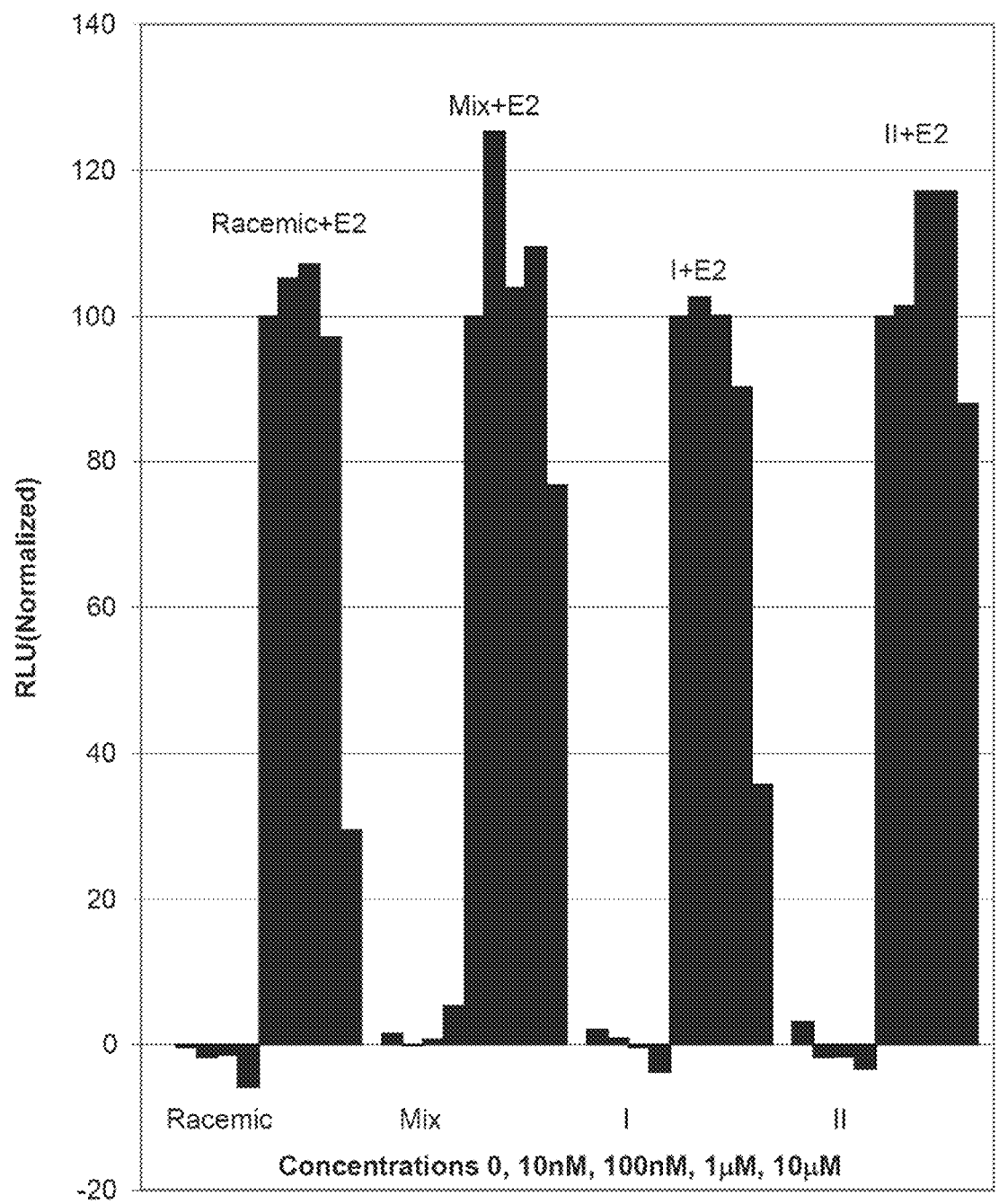
FIG. 10 shows the estrogenic and antiestrogenic activities of representative compounds using an estrogen receptor e-luciferase (ERE-Luciferase) assay.
Figure 11:
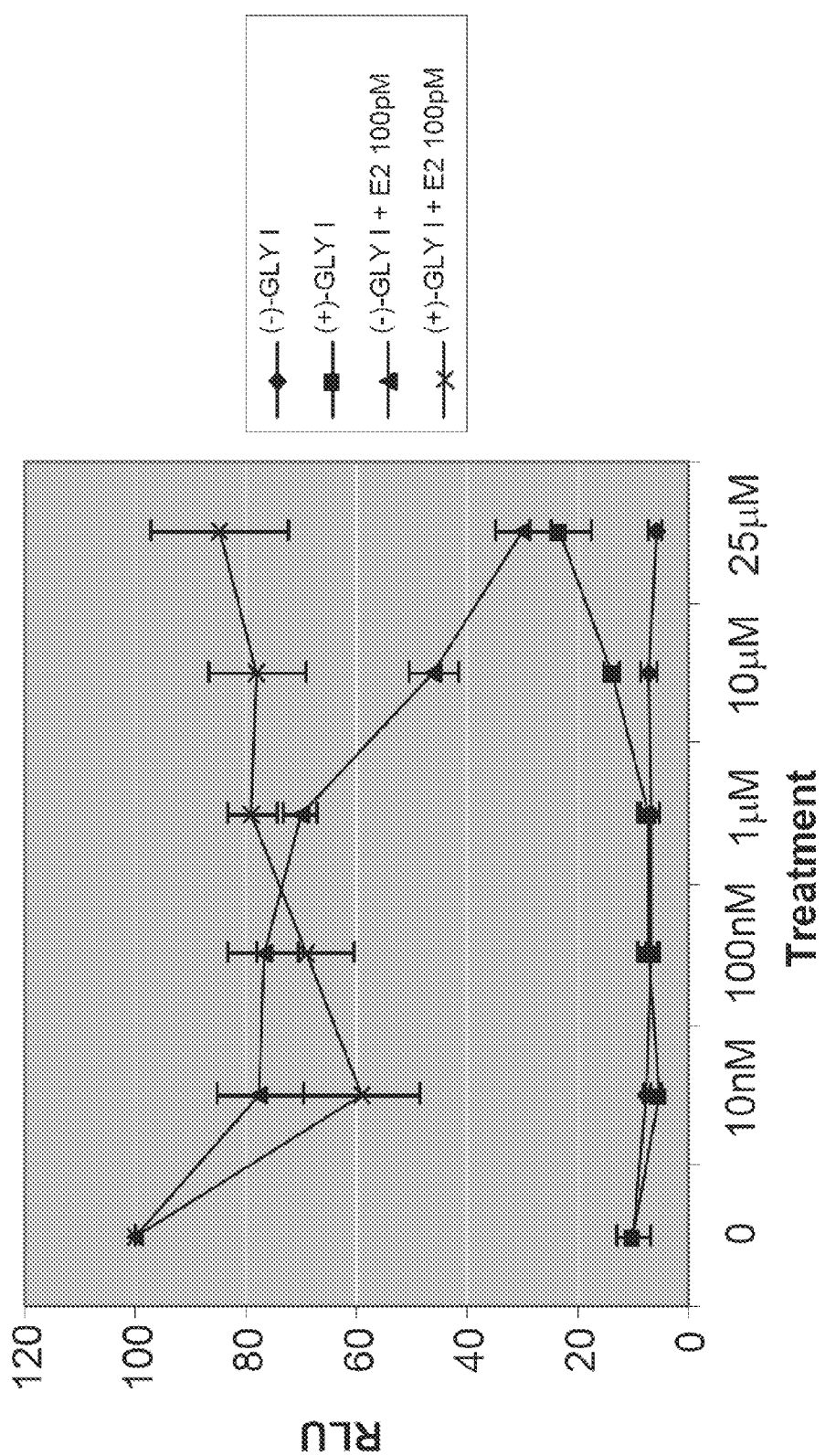
FIG. 11 shows ERE-Luciferase results showing the estrogenic and antiestrogenic activities of synthetic natural (−) GLY I and unnatural (+) GLY I.

Not discernable from this binding screen, however, is whether such interactions will result in either an estrogenic activity (agonist effect), or in an antiestrogenic or inhibitory activity (antagonist effect). Data pertaining to the latter is provided by the inventors' cell culture ERE-Luciferase assay. The results that were observed for this type of assay upon using estrogen receptor positive human breast cancer cells (FIGS. 10 and 11) are quite remarkable. FIG. 10 shows ERE-Luciferase results showing the estrogenic and antiestrogenic activities of synthetic racemic (±) GLY I, isolated glyceollins (I, II, and III), isolated GLY I, and isolated GLY II (E2 at 100 pM). FIG. 11 shows ERE-Luciferase results showing the estrogenic and antiestrogenic activities of synthetic natural (−) GLY I and unnatural (+) GLY I. In these studies, racemic (±) GLY I showed no significant estrogenic activity, and instead displayed strong anti-estrogenic activity at 10 µM. This profile was similar to that observed for both synthesized and soy-isolated natural GLY I, both of which showed only anti-estrogenic activity at 10-25 µM. Alternatively, unnatural (+)-GLY I showed modest estrogenic activity at 10-25 µM, and it demonstrated only slight anti-estrogenic effects in this assay. Glycinol was found to be a significantly stronger estrogenic material.

Equally unanticipated are the remarkable anticancer properties observed for several of the compounds in human breast cancer cell lines that were studied in 10% serum which, by intent, serves to significantly mask estrogen receptor-mediated effects. These results are shown below in Table 2. As in the antioxidant studies, daidzein and genistein were again deployed as standards for comparison purposes. All of the compounds except racemic glycinol, were more potent than genistein which is the better of the two standards in this model (lower dose required to inhibit cell growth by 50% in the MCF7 Column). In most cases this activity was maintained in human breast cancer lines that also have become resistant to many of the clinically used anticancer compounds such as paclitaxel (NCI/ADR-RES Column), while in other cases the fall-off in activity was still minimal compared to that observed for paclitaxel which looses nearly 1,000-fold potency in this multidrug resistant cell line. The one case where the fall-off was the most significant, i.e. ca. 100-fold for the case of the racemic diol 2, likely reflects a strong interaction of this particular material with the P-glycoprotein (Pgp) transporter that is known to be over-expressed in this cell line. One of the most promising and thus very significant features of these compounds is that displayed by the GLYs wherein the inventors found that their desired toxicity (to kill cancer cells) is significantly more potent on the human breast cancer cells (21 and 12 µM in the MCF7 Column) compared to non-cancerous, 'normal' human breast epithelial tissue that is also undergoing rapid cell division (31 and 25 µM in the MCF12A Column). This favorable differential in activity is extremely important from a potential therapeutic point of view. Furthermore, this differential clearly distinguishes these compounds from many of today's anticancer agents presently used within the clinic, e.g. paclitaxel's potency in these two cell lines is nearly equivalent which indicates that there is no differential in its activity, and hence paclitaxel's side-effect toxicities associated with its unwanted actions on normal, rapidly dividing cells. The lack of growth inhibitory activity for the racemic glycinol likely reflects the significantly stronger estrogenic activity of this particular compound as identified in the previous screens. In the present assay, glycinol's growth promoting activity complicates the analysis of any anticancer properties that it may also have. Alternatively, the overall profile displayed by the glycinol analog is demonstrative of a potential selective estrogen receptor modulator or SERM.

TABLE 2

Growth Inhibition of Breast Cancer and Immortalized Normal Breast Tissue Cell Lines

| | | Growth Inhibition Assays | | |
| --- | --- | --- | --- | --- |
| Agent ID | n | MCF7 $GI_{50}$ (μM) | MCF12A $GI_{50}$ (μM) | NCI/ADR-RES $GI_{50}$ (μM) |
| Daidzein | 8 | 200 (190-220) | 120 (110-140) | 150 (140-160) |
| Genistein | 8 | 46 (41-50) | 22 (20-24) | 17 (15-19) |
| 4 (−) | 6 | 7.1 (6.4-7.8) | 11 (9.5-12) | 8.7 (75-9.9) |
| 4 (+) | 6 | 14 (13-15) | 15 (14-16) | 13 (13-14) |
| 4 (+/−) | 6 | 4.1 (3.8-4.5) | 4.0 (3.8-4.1) | 2.9 (2.7-3.1) |
| 7 (+) | 6 | 21 (20-23) | 31 (29-33) | 38 (36-41) |
| 7 (−) | 6 | 12 (11-13) | 25 (24-27) | 27 (26-28) |
| Glycinol (+/−) | 6 | >1000 | >1000 | >1000 |
| 2 (+/−) | 6 | 10 (9.6-11) | 20 (17-22) | 120 (110-130) |
| 3 (+/−) | 6 | 31 (28-35) | 36 (30-43) | 21 (19-23) |

Compound designations are the same as for TABLE 1. Experimental details are provided in the Examples section.

The inventors' in vivo studies further confirmed the promise of these various materials as either anticancer agents or as selective estrogen receptor modulators (SERMs) wherein for the former, human cancer xenographs were established in rodent models. Taken together, all of the biological testing results are mutually supportive of the potential use of various of these materials to prevent or treat human cancers, or for use as SERMs. With regard to the latter, one preferred inventive embodiment includes the use of either (+)-GLY or, in particular, the de-protected intermediate also known as the natural product "glycinol," as SERM therapy to prevent bone loss or to alleviate undesirable menopausal manifestations such as hot flashes and mood swings without increasing the risk of cardiovascular side-effects or increasing the incidences of breast cancer and/or uterine cancer. Another particularly preferred embodiment includes the use of GLY I as a cancer preventative or cancer treatment agent via: (i) its enhancement or direct instillation into natural materials so as to provide fortified food products or medicinal foods; (ii) formulations which can be used as dietary supplements or over-the-counter consumer products like the common vitamin preparations; or (iii) formulations which can be prescribed as ethical pharmaceutical agent products. The latter type of product is also applicable to the use of (+)-GLY for these same types of therapeutic indications, as well as to several of the other materials having novel compositions of matter. A final embodiment takes advantage of the differing estrogenic activities within various of the compound members to be used in a mixed fashion to achieve a pre-selected profile of partial estrogenic agonist and estrogen receptor antagonist properties that can be blended from synthesized natural forms into food and dietary supplement products, or that can be blended from unnatural forms into very unique ethical pharmaceutical agent products.

EXAMPLE 1

Synthesis of glyceollin-related isoflavones and isoflavenes via the general biomimetic route shown in Scheme 2 and in Scheme 1 (Step d) as exemplified by the case where thallium is deployed during ring closure and wherein the distinctly inventive arrangement for the protecting groups is $R^1=R^2=Bn$, $R^3=MOM$, and $R^4$ is initially H which is then converted to acetyl (Ac), all of which is specifically depicted in Scheme 3.

4-Benzyloxy-2-hydroxy-acetophenone

Oven-dried potassium carbonate (1.65 g, 12 mmol) was added to a solution of 2,4-dihydroxy-acetopheneone (1.52 g, 10 mmol) in 10 mL of acetonitrile and the mixture was stirred for one hour at RT. Benzylbromide (1.3 mL, 11 mmol) was added and the mixture was refluxed for 10 hours. After disappearance of 2,4-dihydroxy-acetopheneone (TLC), the solvent was evaporated to one-third volume and poured into ice water with vigorous stirring. A pinkish-white solid precipitated. The solid was recrystallized from methanol (ca. 20 mL) to obtain 2.12 g (88%) of white product: mp 109-110° C. [Lit.(64) 108-109° C.); TLC $R_f$ 0.47 hexanes:EtOAc (5:1), $^1H$ NMR (400 MHz, DMSO-$d_6$) δ 12.56 (s, 1H, OH), 7.80-7.78 (s, 1H, J=8.8 Hz, Ar—H6), 7.38-7.28 (m, 5H, $C_6H_5$), 6.56-6.53 (dd, 1H, $^2J$=8.8 Hz, $^3J$=2.4 Hz, Ar—H5), 6.5 (d, 1H, $^3J$=2.4 Hz, Ar—H3), 5.13 (s, 2H, O—$CH_2$), 2.5 (s, 3H, $CH_3CO$); $^{13}C$ NMR (100 MHz, DMSO-d6) δ 203.9, 165.4, 164.6, 136.9, 134, 129.2, 128.8, 128.5, 114.6, 108.5, 102.4, 70.3, 27.3.

2-Hydroxy-4-methoxymethyloxy-benzaldehyde

Oven-dried potassium carbonate (1.38 g, 10 mmol) was added to an ice cooled solution of 2,4-dihydroxy-benzaldehyde (1.38 g, 10 mmol) in 10 mL of acetone. MOMCl (1.54 mL, 20 mmol) was added drop-wise and the mixture was stirred at 0° C. for one hour, after which it was gradually allowed to come to RT. The reaction was further stirred for 24 hours at RT and then poured into ice water with vigorous stirring. A Buff colored solid precipitated. The solid was filtered, dried and recrystallized from MeOH:DCM (ca. 30:5 mL) to obtain 1.31 g (72%) of white solid: mp 52-53° C. [Lit.(65) 50-51° C.]; TLC $R_f$ 0.43 in hexanes:EtOAc (2:1), $^1$H NMR (400 MHz, CDCl$_3$) δ 11.38 (s, 1H, OH), 9.74 (s, 1H, CHO), 7.46-7.44 (d, 1H, J=8.4 Hz, Ar—H6), 6.66-6.64 (dd, 1H, $^2$J=8.4 Hz, $^3$J=2 Hz, Ar—H5), 6.60 (d, 1H, $^3$J=2 Hz), 5.24 (s, 2H, O—CH$_2$—O), 3.48 (s, 3H, OCH$_3$). $^{13}$C NMR (100 MHz, CDCl$_3$) δ 194.8, 164.5, 164.4, 135.6, 116.2, 109.3, 103.6, 94.3, 56.7.

2-Benzyloxy-4-methoxymethyloxy-benzaldehyde

Oven-dried potassium carbonate (0.272 g, 2 mmol) was added to a solution of 2-hydroxy-4-methoxymethyloxy-benzaldehyde (0.182 g, 1 mmol) in 10 mL of acetonitrile and the mixture was stirred for one hour at RT. Benzylbromide (0.24 mL, 2 mmol) was added and the mixture was refluxed for 10 hours. After disappearance of 2-hydroxy-4-methoxymethybenzaldehyde (TLC), the solvent was evaporated. The residue was chromatographed over silica using hexanes:EtOAC (5:1). The organic fractions were evaporated to obtain 0.218 g (80%) of yellow oil; TLC $R_f$ 0.27 hexanes:EtOAc (5:1), $^1$H NMR (400 MHz, CDCl$_3$) δ 10.4 (s, 1H, CHO); 7.81-7.83 (d, 1H, J=8.4 Hz, Ar—H6); 7.46-7.39 (m, 5H, C$_6$H$_5$); 6.7-6.69 (m, 2H, Ar—H3/Ar—H5); 5.21 (s, 2H, O—CH$_2$—O); 5.16 (s, 2H, PhCH$_2$); 3.48 (s, 3H, OCH$_3$); $^{13}$C NMR (100 MHz, CDCl$_3$) δ 188.6, 163.9, 162.9, 136.1, 130.5, 128.9, 128.5, 127.6, 120.2, 108.8, 101, 94.4, 70.7; analysis calc'd. for C$_{16}$H$_{16}$O$_4$: C, 70.57; H, 5.92; O, 23.5. found: C, 70.35; H, 5.95; O, 23.72.

2-Benzyloxy-4-methoxymethyloxy-4'-benzyloxy-2'-hydroxy-chalcone

A mixture of 2-benzyloxy-4-methoxymethyloxy-benzaldehyde (2.72 g, 10 mmol) and 4-benzyloxy-2-hydroxy-acetophenone (2.42 g, 10 mmol) in 50 mL of anhydrous methanol was refluxed in the presence of piperidine (1 mL, 10 mmol) for ca. 4 hours after which it was cooled to RT. Yellow solid precipitated. The solid was filtered and washed with 100 mL of methanol. The filtrate was reduced to ca. 50 mL and refluxed for 2 hours after-which it provided additional product upon cooling in the refrigerator. The combined yield of yellow solid was 4.16 g (84%): mp 147-148° C., TLC $R_f$ 0.19 in hexanes:EtOAc (5:1); $^1$H NMR (400 MHz, DMSO-d$_6$) δ 8.03-7.99 (d, 1H, J=15.2, CH=), 7.86-7.82 (d, 1H, J=15.2, CH=), 7.90-7.88 (d, 1H, J=8.8 Hz, Ar—H6'), 7.74-7.73 (d, 1H, J=9.2 Hz, Ar—H6), 7.56-7.36 (m, 10H, 2×C$_6$H$_6$), 6.89 (d, 1H, J=2.4 Hz, Ar—H3'), 6.75-6.72 (dd, 1H, $^2$J=8.8 Hz, $^3$J=2.4 Hz, Ar—H5'), 6.58 (d, 1H, $^3$J=2.8 Hz, Ar—H3), 6.50-6.47 (dd, 1H, $^2$J=9.2 Hz, $^3$J=2.4 Hz, Ar—H5), 5.29 (s, 2H, O—CH$_2$), 5.20 (s, 4H, Ph-CH$_2$), 3.40 (s, 3H, OCH$_3$); $^{13}$C NMR (100 MHz, DMSO-d6) δ 192.6, 166.3, 166.4, 161.2, 160, 140.3, 137.1, 136.9, 132.8, 132.5, 129.4, 129.2, 129, 128.8, 128.6, 119.4, 117.6, 114.6, 109, 108.5, 102.6, 102.1, 94.5, 70.9, 70.4, 56.6. analysis calc'd. for C$_{31}$H$_{28}$O$_6$: C, 74.98; H, 5.68; O, 19.33. found: C, 75.01; H, 5.69; O, 19.27.

2-Benzyloxy-4-methoxymethyloxy-4'-benzyloxy-2'-acetoxy-chalcone

To a solution of 2-benzyloxy-4-methoxymethyloxy-4'-benzyloxy-2'-hydroxy-chalcone (0.496 g, 1 mmol), in 10 mL of acetic anhydride was added triethylamine (0.25 mL, 2 mmol) and the solution heated at 60° C. for ca. 6 hrs. After disappearance of starting material (TLC), the hot reaction mixture was poured into ice water:methanol (1:1) ca. 50 mL. A solid precipitated upon vigorous stirring. The solid was filtered, dried and recrystallized from methanol (ca. 15 mL) to obtain 0.495 g (92%) of white solid: mp 94-96° C.; TLC $R_f$ 0.21 in hexanes:EtOAc (3:1); $^1$H NMR (400 MHz, DMSO-d$_6$) δ 7.78-7.75 (m, 2H), 7.71-7.69 (d, 1H, J=8.8 Hz, Ar—H6'), 7.49-7.36 (m, 10+1H, 2×C$_6$H$_6$+Ar—H8), 6.99-6.96 (dd, 1H, $^2$J=8.4 Hz, $^3$J=2.4 Hz, Ar—H5'), 6.90 (d, 1H, J=2.4 Hz, Ar—H3'), 6.85 (d, 1H, J=2 Hz, Ar—H3), 6.72-6.69 (dd, 1H, $^2$J=8.4 Hz, $^3$J=2.4 Hz, Ar—H5), 5.26 (s, 2H, O—CH$_2$), 5.20 (s, 4H, O—CH$_2$), 3.39 (s, 3H, OCH$_3$), 2.18 (s, 3H, CH$_3$CO); $^{13}$C NMR (100 MHz, DMSO-d$_6$) δ 189, 169.5, 162.5, 160.9, 159.6, 151.4, 139.5, 137.2, 136.9, 132.3, 131.7, 129.3, 129.2, 128.8, 128.6, 128.6, 125.2, 123.3, 117.6, 113, 110.8, 109.1, 102.2, 94.5, 70.7, 70.5, 56.6, 21.5; analysis calc'd. for C$_{33}$H$_{30}$O$_7$: C, 73.60; H, 5.61; O, 20.81. found: C, 73.86; H, 5.62; O, 20.79.

2',7-Dibenzyloxy-4'-hydroxy-isoflavone

2-Benzyloxy-4-methoxymethyloxy-4'-benzyloxy-2'-acetoxy-chalcone (0.538 g, 1 mmol) was dissolved in 2 mL methylene chloride and 25 mL of methanol:trimethylorthoformate (1:1) was added, followed by addition of thallium (III) nitrate-trihydrate (0.666 g, 1.5 mmol). After stirring the suspension for 2 hours at RT it became a clear solution with white thallium (I) nitrate precipitating. After stirring for an additional 4 hours the TLC showed complete disappearance of starting chalcone. Solvents were evaporated to reduce the volume to ca. one-third and then 20 mL of DCM was added, followed by the addition of 0.2 g of sodium bisulfite. After stirring for 1 hour, the entire solid was filtered, solvent evaporated and the resulting residue passed through a short column of silica with hexanes:EtOAc (10:1) as eluent. The solvents were evaporated to obtain 0.48 g (80%) of the acetal intermediate as yellowish oil which was directly used in the next step without further purification. Crude acetal (ca. 0.48 g) was dissolved in 10 mL of methanol and refluxed with 2 mL of 1N HCl for about 12 hours. After disappearance of the acetal (TLC), the reaction mixture was poured into ice water (100 mL). A yellowish white solid precipitated. The precipitate was filtered, dried and recrystallized from MeOH:DCM (ca. 15:2 mL) to obtain 0.306 g (68%) of white powder having a yellow tinge: mp 116-117° C.; TLC $R_f$ 0.25 hexanes:EtOAc (1:1); $^1$H NMR (400 MHz, DMSO-d$_6$) δ 9.59 (s, 1H, OH), 8.22 (s, 1H, OCH=), 8.03-8.01 (d, 1H, J=8.8 Hz, Ar—H5), 7.50-7.23 (m, 10+1H, 2×C$_6$H$_5$+Ar—H8), 7.16-7.13 (dd, 1H, $^2$J=9.2 Hz, $^3$J=2.4 Hz, Ar—H6), 7.06-7.04 (d, 1H, J=8 Hz, ArH-6'), 6.5 (d, 1H, J=1.6 Hz, Ar—H3'), 6.43-6.40 (dd, 1H, $^2$J=8.4 Hz, Ar—H5'), 5.27 (s, 2H, Ph-CH$_2$), 5.02 (s, 2H, Ph-CH$_2$). $^{13}$C NMR (100 MHz, DMSO-d$_6$) δ 75.3, 163.2, 159.5, 158.1, 158, 154.8, 138, 136.8, 132.7, 129.2, 128.9, 128.8, 128.7, 128.2, 127.7, 127.6, 123, 118.4, 115.8, 112.5, 108, 102.3, 101, 70.7, 70; analysis calc'd. for C$_{29}$H$_{22}$O$_5$Si.0.25H$_2$O: C, 76.61; H, 4.99; O, 18.0. found: C, 76.69; H, 4.76; O, 17.68.

2',7-Dibenzyloxy-4'-(t-butyldimethylsilyloxy)-isoflavone

To a solution of 2',7-dibenzyloxy-4'-hydroxy-isoflavone (0.450 g, 1 mmol) in 10 mL of DCM was added triethylamine (0.25 mL, 2 mmol) and TBDMSCl (0.225 g, 1.5 mmol). The reaction mixture was stirred at room temperature for ca. 6 hrs. After disappearance of starting material (TLC) the reaction was quenched with 1N HCl (ca. 2 mL). The mixture was extracted with DCM:water (2×10 mL:10 mL). The organic layer was dried over sodium sulfate and evaporated to give 0.507 g (90%) of fluffy, white solid: mp 132-133° C.; TLC $R_f$ 0.89 in hexanes:EtOAc (1:1); $^1$H NMR (400 MHz, DMSO-$d_6$) δ 8.28 (s, 1H, OCH=), 8.04-8.02 (d, 1H, J=8.8 Hz, Ar—H5), 7.50-7.13 (m, 10+3H, $C_6H_5$, Ar—H6, H6', H8), 6.53-6.48 (m, 2H, Ar—H3'/Ar—H5'), 5.27 (s, 2H, Ph-$CH_2$), 5.08 (s, 2H, Ph$CH_2$), 0.93 {s, 9H, Si($CH_3$)$_3$}, 0.16 {s, 6H, Si($CH_3$)$_2$}; $^{13}$C NMR (100 MHz, DMSO-$d_6$) δ 175.1, 163.3, 158.1, 157.9, 157, 155, 137.9, 136.8, 132.7, 129.2, 128.9, 128.8, 128.6, 128.1, 127.7, 127.6, 122.7, 118.4, 115.9, 115.3, 112.1, 105.9, 102.4, 70.8, 70.1, 26.2, 18.6; analysis calcd. for $C_{35}H_{36}O_5Si \cdot 0.25H_2O$: C, 73.78; H, 6.42. found: C, 73.85; H, 6.38.

2',7-Dibenzyloxy-4'-(t-butyldimethylsilyloxy)-isoflav-3-ene

To an ice cooled solution of 2',7-dibenzyloxy-4'-(t-butyldimethylsilyloxy)-isoflavone (0.564 g, 1 mmol) in 10 mL of THF was added 1.6 M lithium borohydride solution in THF (3 mmol) dropwise. The reaction mixture was allowed to come to RT gradually and then stirred for ca. 2 hrs. After disappearance of the starting material (TLC) the reaction was quenched with 1N HCl (pH 4). The reaction was further stirred at room temperature followed by refluxing at 60° C. for ca. 2 hours. The reaction mixture was extracted with DCM:water (2×15 mL:15 mL). The organic layers were combined and washed with 1N $NaHCO_3$ (2×15 mL), dried over sodium sulfate and evaporated at 20° C. to obtain an oily residue. The residue was chromatographed over silica using DCM:hexanes (1:1). The organic fractions were evaporated to provide 0.247 g (45%) of white solid: mp 105-107° C.; TLC $R_f$ 0.75 in DCM:hexanes (2:1); $^1$H NMR (400 MHz, DMSO-$d_6$) δ 7.46-7.32 (m, 10H, 2×$CH_5$), 7.22-7.20 (d, 1H, J=8.4 Hz, Ar—H5), 7.03-7.01 (d, 1H, J=8.4 Hz), 6.63 (s, 1H, CH=), 6.58-6.55 (m, 2H, Ar—H3'/H5'), 6.49-6.46 (m, 2H, Ar—H6/8), 5.11 (s, 2H, Ph-$CH_2$), 5.07 (s, 2H, Ph-$CH_2$), 4.89 (s, 2H, $OCH_2$), 0.93 {s, 9H, Si($CH_3$)$_3$}, 0.17 {s, 6H, Si($CH_3$)$_2$}; $^{13}$C NMR (100 MHz, DMSO-$d_6$) δ 199.6, 159.7, 157.5, 156.8, 154.7, 137.7, 137.5, 129.7, 129.2, 129.1, 128.6, 128.5, 128.4, 128.3, 128.1, 121.5, 121.4, 117.5, 112.8, 108.9, 105.9, 102.8, 70.5, 69.9, 68.3, 26.3, 18.7; analysis calcd. for $C_{35}H_{38}O_4Si \cdot 0.25H_2O$: C, 75.71; H, 6.99. found: C, 76.0; H, 6.70.

EXAMPLE 2

Synthesis of glyceollin-related isoflavenes via the uniquely-inventive, general non-biomimetic route shown in Scheme 1 (Step g), and as specifically exemplified by the distinct display of R groups and chemical steps depicted in Scheme 4.

2-Benzyloxy-4-methoxymethyloxy-acetophenone

Oven-dried potassium carbonate (0.166 g, 1.2 mmol) was added to an ice cooled solution of 2,4-dihydroxy-acetophenone (0.152 g, 1 mmol) in 5 mL of acetone. MOMCl (0.15 mL, 2 mmol) was added drop-wise and the mixture was stirred at 0° C. for one hour. The temperature of the reaction was gradually allowed to come to RT and further stirred for 24 hours, after which it was quenched with water (ca. 10 mL). The acetone was evaporated under vacuum. The remaining water layer was extracted with DCM (2×10 mL). The organic layers were combined, dried over sodium sulfate and evaporated to obtain 0.156 g (79%) of oily product having a pink tinge. The crude product was used directly in the next step without further purification. The crude product (ca. 0.156 g) was dissolved in 10 mL of acetone. Oven dried potassium carbonate (0.166 g, 1.2 mmol) was added and the mixture stirred for 15 minutes. Benzylbromide (1.3 mL, 11 mmol) was added and the mixture was refluxed for 12 hours. After disappearance of starting material (TLC), the reaction was poured into ice water with vigorous stirring. A pinkish-white solid precipitated and it was recrystallized from methanol (ca. 2 mL) to obtain 0.203 g (71%) of white powder: mp 70-71° C.; TLC $R_f$ 0.32 in hexanes:EtOAc (5:1); $^1$H NMR (600 MHz, $CDCl_3$) δ 7.83-7.82 (d, 1H, Ar—H6), 7.46-7.36 (m, 5H, $C_6H_5$), 6.69-6.66 (m, 2H, Ar—H5/Ar—H3). 5.2, 5.1 (2×s.2× 2H, Ph$CH_2$, O—$CH_2$—O), 3.47 (s, 3H, $OCH_3$), 2.56 (s, 3H, $CH_3CO$); $^{13}$C NMR (100 MHz, $CDCl_3$) δ 198.1, 162.2, 160.2, 136.2, 132.7, 128.9, 128.5, 127.9, 122.6, 108.3, 101.2, 94.5, 70.9, 56.5, 32.4; analysis calcd. for $C_{17}H_{18}O_4$: C, 71.31; H, 6.34. found: C, 71.08; H, 6.40.

4-Bezyloxy-2-hydroxy-benzaldehyde

Anhydrous sodium bicarbonate (0.1 g, 1.2 mmol) was added to a solution of 2,4-dihydroxy-benzaldehyde (0.138 g, 1 mmol) in 10 mL of acetonitrile and the mixture was stirred for 1 hour at RT. Benzylbromide (0.13 mL, 1.1 mmol) was added and the mixture was refluxed for 6 hours. After disappearance of the reactant (TLC), the reaction was poured into ice water with vigorous stirring. A white solid precipitated and it was recrystallized from methanol (ca. 4 mL) to obtain 0.182 g (80%) of white powder: mp 78-80° C.; TLC $R_f$ 0.88 in toluene:methanol (10:1); $^1$H NMR (600 MHz, acetone-$d_6$) δ 11.41 (s, 1H, OH), 9.81 (s, 1H, CHO), 7.68-7.67 (d, 1H, J=8.4 Hz, Ar—H6), 7.45-7.35 (m, 5H, $C_6H_5$), 6.71-6.69 (dd, 1H, $^2$J=8.4 Hz, $^3$J=2.4 Hz, Ar—H5), 6.56 (d, 1H, J=1.8 Hz, Ar—H3), 5.24 (s, 2H, Ph$CH_2$); $^{13}$C NMR (100 MHz, acetone-$d_6$) 194.61, 166.1, 164.4, 135.9, 128.9, 128.6, 127.8, 115.5, 109.1, 101.8, 70.6; analysis calcd. for $C_{14}H_{12}O_3$: C, 73.67; H, 5.30. found: C, 73.62; H, 5.35.

1-[2-Benzyloxy-4-(methoxymethyloxy)-phenyl]-2-iodo-ethanone

2-Benzyloxy-4-methoxymethyloxy-acetophenone (0.286 g, 1 mmol) was dissolved in 1 mL DCM and 5 mL of anhydrous methanol. Selectfluor™ (0.230 g, 0.6 mmol) and elemental iodine (0.126 g, 0.5 mmol) were added and the mixture stirred at room temperature for 12 hours. Then 15 mL of chloroform was added and an ash colored solid precipitated. The precipitate was filtered and the filtrate was extracted with 10% aqueous sodium thiosulfate solution (5×20 mL) until the organic layer became lemon yellow. The organic layer was evaporated under vacuum to obtain a yellowish oily residue which was redissolved in methanol:acetone (ca. 20 mL:2 mL) and refrigerated overnight. The desired product precipitated while the filtrate retained side products having iodination on the aromatic ring and di-iodination at the alpha-carbon. The product was filtered and dried to obtain 0.288 g (70%) of white powder which turned yellow on storage: mp 66-68° C.; TLC $R_f$ 0.29 in hexanes:EtOAc (2:1); $^1$H NMR (600 MHz, $CDCl_3$) δ 7.89-7.88 (d, 1H, J=9 Hz, Ar—H6), 7.50-7.38 (m, 5H, $C_6H_5$), 6.72-6.70 (m, 2H, Ar—H5/Ar—H3), 5.20-5.17 (2×s, 2×2H, Ph$CH_2$/O—$CH_2$—O), 4.4 (s, 2H, $CH_2I$), 3.48 (s, 3H, $OCH_3$); $^{13}$C NMR (100 MHz, $CDCl_3$) δ 192.6, 163.0, 159.9, 135.7, 134.1, 129, 128.8, 128.3, 128.1, 118.5, 108.8, 101, 94.5, 71.3, 56.6; analysis calcd. for $C_{17}H_{17}O_4I$. C, 49.53; H, 4.16; I, 30.79. found: C, 49.41; H, 4.04; I, 30.98.

4-Benzyloxy-salicylalcohol

To an ice cooled suspension of 4-benzyloxy-2-hydroxybenzaldehyde (0.228 g, 1 mmol) in 10 mL of methanol was slowly added sodium borohydride (0.038 g, 1 mmol). After addition of sodium borohydride, a clear solution was obtained. The reaction was stirred at 0° C. for 20 minutes followed by stirring at RT for 10 minutes. The solvent was evaporated under vacuum. To this solid residue was carefully added 0.1 N $H_2SO_4$ until the pH dropped to 6.5 with vigorous stirring. Additional water (ca. 40 mL) was added with continuous stirring which then caused the product to precipitate. The solid was filtered and copiously washed with water to remove all traces of acid (last wash pH>7). The solid was immediately vacuum dried to obtain 0.175 g (76%) white solid: mp 88-90° C.; TLC, $R_f$ 0.29, in hexanes:EtOAc (2:1); $^1$H NMR (600 MHz, DMSO-$d_6$) δ, 9.36 (s, 1H, Ph-OH), 7.43-7.32 (m, 5H, $C_6H_5$), 7.14-7.12 (d, 1H, J=8.4 Hz, Ar—H6), 6.44-6.41 (m, 2H, Ar—H5/Ar—H3), 5.01 (s, 2H, PhCH$_2$), 4.8 (t, 1H, CH$_2$OH), 4.39 (s, 2H, CH$_2$OH); $^{13}$C NMR (100 MHz, DMSO-$d_6$) δ 158.0, 155.2, 137.3, 128.5, 128.4, 128.3, 127.6, 127.5, 127.3, 121.2, 104.8, 101.8, 68.9, 57.9; analysis calcd. for $C_{14}H_{14}O_3$. C, 73.03; H, 6.13. found: C, 73.16; H, 5.94.

2-(5-Benzyloxy-2-hydroxymethyl-phenoxy)-1-(2-benzyloxy-4-methoxymethyloxy-phenyl)-ethanone Potassium carbonate (0.165 g, 1.2 mmol) was added to a solution of 1-[2-benzyloxy-4-(methoxymethyloxy)phenyl]-2-iodo-ethanone (0.412 g, 1 mmol) and 4-benzyloxy-salicylalchohol (0.254 g, 1.1 mmol) in 10 mL of acetone and the mixture refluxed for 10 hours. After completion of the reaction (TLC), the solvent was evaporated and the residue extracted with EtOAc:water (2×20 mL:20 mL). The organic layers were combined, dried over sodium sulfate and evaporated. The residue was chromatographed over silica using hexanes:EtOAc (2:1). The organic fractions were evaporated to provide 0.371 g (72%) of white solid: mp 115-118° C.; TLC $R_f$ 0.16 in hexanes:EtOAc (2:1); $^1$H NMR (600 MHz, CDCl$_3$) δ 7.88-7.86 (d, 1H, J=9 Hz, Ar—H5), 7.64-7.25 (m, 10H, 2×$C_6H_5$), 7.21-7.20 (d, 1H, J=8.4 Hz, Ar—H6'), 6.92 (d, 1H, J=2.4 Hz, Ar—H8), 6.78-6.76 (dd, 1H, $^2$J=9 Hz, $^3$J=2.4 Hz, Ar—H6), 6.56-6.54 (dd, 1H, $^2$J=8.4 Hz, $^3$J=2.4 Hz, Ar—H5'), 6.26-6.25 (d, 1H, J=2.4 Hz, Ar—H3'), 5.30 (s, 4H, PhCH$_2$), 5.21 (s, 2H, O—CH$_2$—O), 4.98 (s, 2H, H-2), 4.57-4.56 (d, 2H, J=6 Hz, CH$_2$OH), 4.13-4.11 (t, 1H, CH$_2$OH), 3.44 (s, 3H, OCH$_3$); $^{13}$C NMR (100 MHz, CDCl$_3$) δ 194.6, 164.4, 162.2, 160.7, 158.6, 138.9, 137.6, 133.6, 130.2, 129.9, 129.8, 129.2, 125.1, 120.4, 110, 106.8, 102.5, 101.7, 95.6, 75.3, 72.4, 71.2, 61.5, 56.9; analysis calcd. for $C_{31}H_{30}O_7$. C, 72.36; H, 5.88. found: C, 72.1; H, 5.85.

2',7-Dibenzyloxy-4'-methoxymethyloxy-isoflav-3-ene

To a solution of 2-(5-Benzyloxy-2-hydroxymethyl-phenoxy)-1-(2-benzyloxy-4-methoxymethyloxy-phenyl)-ethanone (0.514 g, 1 mmol) in 5 mL of acetonitrile was added triphenyl phosphine hydrobromide (0.343 g, 1 mmol) and the suspension stirred at RT for ca. 4 hours. After disappearance of starting material (TLC), organic solvent was evaporated at 20° C. to provide a yellowish solid. The solid was redissolved in 5 mL of DCM and anhydrous ether was added with constant stirring. The white Wittig's ylide precipitated. This product was used directly in the next step without further purification. The crude product (ca. 0.80 g) was dissolved in 10 mL of methanol followed by addition of sodium methoxide (0.108 g, 2 mmol). The suspension was refluxed for ca. 12 hours after which it was allowed to come to RT. A white solid precipitated. The precipitate was filtered and the filtrate was concentrated to ca. one-half the volume and again refluxed for 4 hours after which it provided additional product upon cooling to RT. The combined product was recrystallized from methanol (ca. 30 mL) to obtain 0.374 g (78%) of white solid: mp 132-134° C.; TLC $R_f$ 0.43, in hexanes:EtOAc (5:1); $^1$H NMR (600 MHz, acetone-$d_6$) δ 7.51-7.31 (m, 10H, 2×$C_6H_5$), 7.28-7.27 (d, 1H, J=8.4 Hz, Ar—H5), 7.01-7.00 (d, 1H, J=7.8 Hz, Ar—H6'), 6.8 (d, 1H, J=2.4 Hz, Ar—H8), 6.69-6.67 (dd, 1H, $^2$J=8.4 Hz, $^3$J=2.4 Hz, Ar—H6), 6.60 (s, 1H, Ar—H4), 6.57-6.55 (dd, 1H, $^2$J=8.4 Hz, $^3$J=2.4 Hz, Ar—H5'), 6.46 (d, 1H, J=2.4 Hz, Ar—H3'), 5.2 (s, 2H, O—CH$_2$—O), 5.13 (s, 2H, PhCH$_2$), 5.09 (s, 2H, PhCH$_2$), 4.92 (s, 2H, H2), 3.42 (s, 3H, OCH$_3$); $^{13}$C NMR (100 MHz, acetone-$d_6$) δ 161.1, 159.9, 158.9, 156.3, 138.9, 138.5, 130.6, 130.5, 130, 129.9, 129.4, 129.3, 129.2, 129, 128.9, 123.2, 122.6, 118.8, 109.6, 103.6, 103.2, 95.8, 71.8, 71.1, 69.6, 56.7; analysis calcd. for $C_{31}H_{28}O_5$. C, 77.01; H, 5.80. found: C, 77.0; H, 5.80.

2',7-Dibenzyloxy-4'hydroxy-isoflav-3-ene

To a solution of 2',7-dibenzyloxy-4'-methoxymethyloxy-isoflav-3-ene (0.480 g, 1 mmol) in acetonitrile:water (20 mL:1 mL) was added triphenyl phosphine hydrobromide (0.788 g, 2 mmol). The reaction was heated to 50° C. for ca. 2 hrs. After disappearance of the starting material (TLC), the solvent was evaporated at 20° C. The residue was extracted with EtOAc:water (3×10 mL:10 mL). The organic layers were combined, dried and evaporated. The residue was chromatographed over silica using hexanes:EtOAc (5:1). The organic fractions were evaporated to provide 0.374 g (78%) of product as an oil. Because of the instability of this intermediate, it was immediately used for the next step: TLC $R_f$ 0.43, in hexanes:EtOAc (5:1); $^1$H NMR (600 MHz, DMSO-$d_6$) δ 9.66 (s, 1H, OH), 7.46-7.32 (m, 10H, 2×CH$_5$), 7.14, 7.13 (d, 1H, J=8.4 Hz, Ar—H5), 7.01-6.99 (d, 1H, J=7.8 Hz, Ar—H6') 6.57-6.55 (m, 2H, H4/Ar—H5'), 6.59-6.52 (d, 1H, J=2.4 Hz, Ar—H8), 6.48-6.47 (d, 1H, J=2.4 Hz, Ar—H3'), 6.41-6.39 (dd, 1H, $^2$J=8.4 Hz, $^3$J=2.4 Hz, Ar—H5'), 5.07 (s, 4H, PhCH$_2$), 4.85 (s, 2H, H2).

2',7-Dibenzyloxy-4'-(t-butyldimethylsilyloxy)-isoflav-3-ene

To a solution of 2',7-(dibenzyloxy)-4'-hydroxy-isoflav-3-ene (0.374 g, 0.8 mmol) in DCM was added TBDMSCl (0.180 g, 1.2 mmol) and triethylamine (0.2 mL, 1.5 mmol). The reaction mixture was stirred for 12 hours. After disappearance of reactant (TLC), the reaction was quenched with saturated ammonium chloride solution (10 mL) and the resulting mixture extracted with DCM:water (3×10 mL:10 mL) The organic layers were combined, dried over sodium sulfate and evaporated to give white product. The crude product was recrystallized from DCM:methanol (ca. 5:25 mL) to obtain 0.370 g (69% for two steps) of white crystals: mp 106-107° C.; TLC $R_f$ 0.75 in DCM:hexanes (2:1); $^1$H NMR (400 MHz, DMSO-$d_6$) δ 7.46-7.32 (m, 10H, 2×CH$_5$), 7.22-7.20 (d, 1H, J=8.4 Hz, Ar—H5), 7.03-7.01 (d, 1H, J=8.4 Hz), 6.58-6.55 (m, 2H, Ar—H3'/H5), 6.49-6.46 (m, 2H, Ar—H6/8), 5.11 (s, 2H, Ph-CH$_2$), 5.07 (s, 2H, Ph-CH$_2$), 4.89 (s, 2H, OCH$_2$), 0.93 {s, 9H, Si(CH$_3$)$_3$}, 0.17 {s, 6H, Si(CH$_3$)$_2$}; $^{13}$C NMR (100 MHz, DMSO-$d_6$) δ199.6, 159.7, 157.5, 156.8, 154.7, 137.7, 137.5, 129.7, 129.2, 129.1, 128.6, 128.5, 128.4, 128.3, 128.1, 121.5, 121.4, 1117.5, 112.8, 108.9. 105.9, 102.8, 70.5, 69.9, 68.3, 26.3, 18.7; analysis calcd. for C$_{35}$H$_{38}$O$_4$Si, C, 75.71; H, 6.99. found: C, 75.41; H, 6.70.

EXAMPLE 3

Synthesis of the glyceollin-related 3,4-diols as exemplified by the preferred embodiments and distinct methodological steps specifically depicted in Scheme 5 (Steps a and b).

(+) 4'-(t-Butyldimethylsilyloxy)-2',7-dibenzyloxy-isoflavan-3,4-diol

2',7-Dibenzyloxy-4'-t-butyldimethylsilyloxy-isoflav-3-ene (0.537 g, 1 mmol) was dissolved in 10 mL of acetone and 1 mL of water was added. Methane sulfonamide (0.095 g, 1 mmol) and 4-Methylmorpholine-4-oxide i.e. NMO (0.140 g, 1.2 mmol) were then added and the resulting mixture stirred at 0° C. for 30 minutes. Osmium tetroxide solution in water (1 mL=0.004 mmol) was added slowly, upon which the reaction turned brownish-yellow. The reaction was gradually allowed to come to RT and stirred for 24 hours. After disappearance of the reactant (TLC), the reaction was quenched with 1 g of sodium bisulfate followed by evaporation of acetone. The residue was extracted with EtOAc:water (2×10 mL:10 mL). The organic layers were combined, dried over sodium sulfate, filtered and evaporated. The residue was chromatographed over silica with hexanes:EtOAc (5:1). The organic fractions were evaporated to provide 0.525 g (90%) of fluffy, white solid: mp 110-112° C.; TLC R$_f$ 0.25 in hexanes:EtOAc (5:1); $^1$H NMR (400 MHz, acetone-d$_6$) δ 7.46 (d, 1H, J=8.4 Hz, Ar—H5), 7.46-7.28 (m, 10+1H, 2×C$_6$H$_5$+Ar—H6'), 6.58-6.56 (m, 2H, Ar—H8/Ar—H5'), 6.49-6.47 (q, 1H, J=8.4 Hz, J=1.8 Hz, Ar—H6), 6.37 (d, 1H, J=2.8 Hz, Ar—H3'), 5.51 (d, 1H, J=7.2, H4), 5.19 (s, 2H, PhCH$_2$), 5.06 (s, 2H, PhCH$_2$), 4.73-4.71 (d, 1H, J=11.4, H-2 eq), 4.24-4.23 (d, 1H, J=7.24, 4-OH), 4.19 (s, 1H, 3-OH), 4.03-4.00 (d, 1H, J=11.4 Hz, H2 ax), 0.96 {s, 9H, Si(CH$_3$)$_3$}, 0.17 {s, 6H, Si(CH$_3$)$_2$}; $^{13}$C NMR (100 MHz, acetone-d$_6$) δ 160.6, 158.2, 157.9, 156.4, 139.1, 138.6, 131.5, 130.8, 130.1, 129.9, 129.3, 129.1, 128.9, 128.8, 124.2, 119.1, 113.2, 109.4, 106.9, 102.8, 72.7, 71.6, 70.9, 68.3, 26.6, 19.3; analysis calcd. for C$_{35}$H$_{40}$O$_6$Si. C, 71.89; H, 6.89. found: C, 71.72; H, 6.81.

(−) 4'-(t-Butyldimethylsilyloxy)-2',7-dibenzyloxy-isoflavan-3,4-diol

To a solution of 2',7-dibenzyloxy-4'-t-butyldimethylsilyloxy-isoflav-3-ene (0.537 g, 1 mmol) in 5 mL of DCM cooled at −78° C. was added chiral catalyst (DHQD)$_2$PHAL i.e. hydroquinidine-1,4-phthalazinediyl diether (0.78 g, 1 mmol), and the mixture stirred for 20 minutes. Osmium tetroxide (0.254 g 1 mmol) was slowly added upon which the reaction turned brownish-yellow. The reaction was stirred for 24 hours. After disappearance of the reactant (TLC), the reaction was quenched with 2 g of sodium bisulfate followed by extraction with EtOAc:water (2×10 mL:10 mL). The organic layers were combined, dried over sodium sulfate, filtered and evaporated. The residue was chromatographed over silica with hexanes:EtOAc (5:1). The organic fractions were evaporated to provide 0.41 g (70%) as a fluffy, white solid: mp 110-113° C.; TLC R$_f$ 0.25 in hexanes:EtOAc (5:1); $^1$H NMR (400 MHz, acetone-d$_6$) δ 7.46 (d, 1H, J=8.4 Hz, Ar—H5), 7.46-7.28 (m, 10+1H, 2×C$_6$H$_5$+Ar—H6'), 6.58-6.56 (m, 2H, Ar—H8/Ar—H5'), 6.49-6.47 (q, 1H, J=8.4 Hz, J=1.8 Hz, Ar—H6), 6.37 (d, 1H, J=2.8 Hz, Ar—H3'), 5.51 (d, 1H, J=7.2, H4), 5.19 (s, 2H, PhCH$_2$), 5.06 (s, 2H, PhCH$_2$), 4.73-4.71 (d, 1H, J=11.4, H-2 eq), 4.24-4.23 (d, 1H, J=7.24, 4-OH), 4.19 (s, 1H, 3-OH), 4.03-4.00 (d, 1H, J=11.4 Hz, H2 ax), 0.96 {s, 9H, Si(CH$_3$)$_3$}, 0.17 {s, 6H, Si(CH$_3$)$_2$}.

(+) 4'-(t-Butyldimethylsilyloxy)-2',7-dibenzyloxy-isoflavan-3,4-diol

To a solution of 2',7-dibenzyloxy-4'-t-butyldimethylsilyloxy-isoflav-3-ene (0.532 g, 1 mmol) in 5 mL of DCM cooled at −78° C. was added chiral catalyst (DHQ)$_2$PHAL i.e. hydroquinine-1,4-phthalazinediyl diether (0.78 g, 1 mmol) and the mixture stirred for 20 minutes. Osmium tetroxide (0.254 g, 1 mmol) was added upon which the reaction turned brownish-yellow. The reaction was stirred for 24 hours. After disappearance of the reactant (TLC), the reaction was quenched with 2 g of sodium bisulfate followed by extraction with EtOAc:water (2×10 mL:10 mL). The organic layers were combined, dried over sodium sulfate, filtered and evaporated. The residue was chromatographed over silica with hexanes:EtOAc (5:1). The organic fractions were evaporated to provide 0.385 g (66%) of fluffy, white solid: mp 110-112° C.; TLC R$_f$ 0.25 in hexanes:EtOAc (5:1); $^1$H NMR (400 MHz, acetone-d$_6$) δ 7.46 (d, 1H, J=8.4 Hz, Ar—H5), 7.46-7.28 (m, 10+1H, 2×C$_6$H$_5$+Ar—H6'), 6.58-6.56 (m, 2H, Ar—H8/Ar—H5'), 6.49-6.47 (q, 1H, J=8.4 Hz, J=1.8 Hz, Ar—H6), 6.37 (d, 1H, J=2.8 Hz, Ar—H3'), 5.51 (d, 1H, J=7.2, H4), 5.19 (s, 2H, PhCH$_2$), 5.06 (s, 2H, PhCH$_2$), 4.73-4.71 (d, 1H, J=11.4, H-2 eq), 4.24-4.23 (d, 1H, J=7.24, 4-OH), 4.19 (s, 1H, 3-OH), 4.03-4.00 (d, 1H, J=11.4 Hz, H2 ax), 0.96 {s, 9H, Si(CH$_3$)$_3$}, 0.17 {s, 6H, Si(CH$_3$)$_2$}.

General Procedure for Debenzylation

To a solution of 4'-t-butyldimethylsilyloxy-2',7-dibenzyloxyisoflavan-3,4-diol (0.584 g, 1 mmol) in 6 mL of acetone was added 10% Pd—C (0.1 g) in 4 mL of cold acetone. This reaction mixture was hydrogenated at room temperature under 1 atm (15 psi) of H$_2$ pressure for ca. 4 hours. After the disappearance of starting material (TLC), the catalyst was filtered through a pad of celite. The celite-pad was washed with 10×2 mL of methanol. The solution was filtered once more through filter paper and evaporated to obtain the solids specified below.

(+) 4'-(t-Butyldimethylsilyloxy)-2',7-dihydroxy-isoflavan-3,4-diol

White solid with red tinge: 0.360 g (89%); mp decomposes at 142° C.; TLC R$_f$ 0.23 in hexanes:EtOAc (2:1); $^1$H NMR (400 MHz, acetone-d$_6$) δ 7.21-7.20 (d, 1H, J=8.4 Hz, Ar—H5), 7.18-7.17 (d, 1H, J=8.4 Hz, Ar—H6'), 6.43-6.41 (dd, 1H, $^2$J=8.4 Hz, $^3$J=2.4 Hz, Ar—H6), 6.34 (d, 1H, J=2.4 Hz, Ar—H8), 6.29-6.28 (dd, 1H, $^2$J=8.4 Hz, $^3$J=2.4 Hz, Ar—H5'), 6.26 (d, 1H, J=2.4 Hz), 5.09 (s, 1H, H4), 4.36-4.34 (d, 1H, J=11.4, H2 eq), 4.14-4.12 (d, 1H, J=11.4 Hz, 4-OH), 4.19 (s, 1H, 3-OH), 4.03-4.00 (d, 1H, J=11.4 Hz, H2 ax), 0.96 {s, 9H, Si(CH$_3$)$_3$}, 0.18 {s, 6H, Si(CH$_3$)$_2$}, $^{13}$C NMR (100 MHz, acetone-d$_6$) δ 159.5, 150.8, 157.7, 155.9, 132.0, 129.0, 120.5, 116.7, 112.3, 110, 109.7, 103.4, 73.9, 70.1, 69.1, 26.5, 19.2; analysis calcd. for C$_{21}$H$_{28}$O$_6$Si. C, 62.35; H, 6.98. found: C, 62.38; H, 7.01.

(−) 4'-(t-Butyldimethylsilyloxy)-2',7-dihydroxy-isoflavan-3,4-diol

White solid with red tinge: 0.34 g (84%); mp decomposes at 144° C.; TLC R$_f$ 0.23 in hexanes:EtOAc (2:1); $^1$H NMR (400 MHz, acetone-d$_6$) δ 7.21-7.20 (d, 1H, J=8.4 Hz, Ar—H5), 7.18-7.17 (d, 1H, J=8.4 Hz, Ar—H6'), 6.43-6.41 (dd, 1H, $^2$J=8.4 Hz, $^3$J=2.4 Hz, Ar—H6), 6.34 (d, 1H, J=2.4

Hz, Ar—H8), 6.29-6.28 (dd, 1H, $^2J$=8.4 Hz, $^3J$=2.4 Hz, Ar—H5'), 6.26 (d, 1H, J=2.4 Hz), 5.09 (s, 1H, H4), 4.36-4.34 (d, 1H, J=11.4, H-2 eq), 4.14-4.12 (d, 1H, J=11.4 Hz, 4-OH), 4.19 (s, 1H, 3-OH), 4.03-4.00 (d, 1H, J=11.4 Hz, H2 ax), 0.96 {s, 9H, Si(CH$_3$)$_3$}, 0.18 {s, 6H, Si(CH$_3$)$_2$}.

(+) 4'-(t-Butyldimethylsilyloxy)-2',7-dihydroxy-isoflavan-3,4-diol

White solid with red tinge: 0.364 g (90%); mp decomposes at 142° C.; TLC R$_f$0.23 in hexanes:EtOAc (2:1); $^1$H NMR (400 MHz, acetone-d$_6$) δ 7.21-7.20 (d, 1H, J=8.4 Hz, Ar—H5), 7.18-7.17 (d, 1H, J=8.4 Hz, Ar—H6'), 6.43-6.41 (dd, 1H, $^2J$=8.4 Hz, $^3J$=2.4 Hz, Ar—H6), 6.34 (d, 1H, J=2.4 Hz, Ar—H8), 6.29-6.28 (dd, 1H, $^2J$=8.4 Hz, $^3J$=2.4 Hz, Ar—H5'), 6.26 (d, 1H, J=2.4 Hz), 5.09 (s, 1H, H4), 4.36-4.34 (d, 1H, J=11.4, H-2 eq), 4.14-4.12 (d, 1H, J=11.4 Hz, 4-OH), 4.19 (s, 1H, 3-OH), 4.03-4.00 (d, 1H, J=11.4 Hz, H2 ax), 0.96 {s, 9H, Si(CH$_3$)$_3$}, 0.18 {s, 6H, Si(CH$_3$)$_2$}.

EXAMPLE 4

Closure of the benzofuran ring within glyceollin-related compounds as exemplified by the specific and unique method depicted in Scheme 5 (Step c).

General Procedure

To a solution of 4'-t-butyldimethylsilyloxy-2',7-dihydroxyisoflavan-3,4-diol (0.041 g, 0.1 mmol) in 20 mL of anhydrous ethanol was added (4 mg, 0.01 mmol) 1,3,4,6,7,8-hexahydro-2H-pyrimido[1,2-a]pyrimidine, polymer-bound and 4 Å molecular sieves (0.1 g). The reaction mixture was refluxed at 80° C. for 6 hours with continuous distillation of the ethanol-water azeotrope. After disappearance of reactant (TLC), the molecular sieves and polymeric base were filtered. The filtrate was dried over sodium sulfate, filtered and solvent evaporated at 20° C. The residue was chromatographed over silica using hexanes:EtOAc (4:1). The organic fractions were evaporated at 20° C. to provide the solids specified below.

(+) 9-(t-Butyldimethylsilyloxy)-glycinol

Pinkish-white solid: 0.023 g (60%); mp 197-199° C.; TLC R$_f$0.38 in hexanes:EtOAc (2:1); $^1$H NMR (400 MHz, acetone-d$_6$) δ 8.55 (s. 1H, —OH), 7.31-7.29 (d, 1H, J=8.4 Hz, Ar—H1), 7.26-7.25 (d, 1H, J=8.4, Ar—H7), 6.56-6.54 (dd, 1H, $^2J$=8.4 Hz, $^3J$=2.4 Hz, Ar—H-2), 6.46-6.44 (dd, 1H, $^2J$=8.4 Hz, $^3J$=2.4 Hz, Ar—H8), 6.3 (d, 1H, J=2.4 Hz, ArH-4), 6.26 (d, 1H, J=2.4 Hz, ArH-10), 5.26 (s, 1H, 11a-H), 5.01 (s, 1H, 6a-OH), 4.14 (d, 1H, J=12 Hz H6 eq), 4.02 (d, 1H, J=12 Hz, H6 ax), 0.96 {s, 9H, Si(CH$_3$)$_3$}, 0.19 {s, 6H, Si(CH$_3$)$_2$}; $^{13}$C NMR (100 MHz, acetone-d$_6$) δ 162.4, 160.3, 159.3, 157.7, 133.8, 125.6, 124.3, 114.1, 113.8, 111.4, 104.5, 103.9, 86.6, 77.4, 71.3, 26.6, 19.3; analysis calcd. for C$_{21}$H$_{26}$O$_5$Si. C, 65.26; H, 6.78. found: C, 65.10; H, 6.67.

(−) 9-(t-Butyldimethylsilyloxy)-glycinol

Pinkish-white solid: 0.025 g (64%); mp 198-200° C.; TLC R$_f$0.38 in hexanes:EtOAc (2:1); $^1$H NMR (400 MHz, acetone-d$_6$) δ 8.55 (s. 1H, —OH), 7.31-7.29 (d, 1H, J=8.4 Hz, Ar—H1), 7.26-7.25 (d, 1H, J=8.4, Ar—H7), 6.56-6.54 (dd, 1H, $^2J$=8.4 Hz, $^3J$=2.4 Hz, Ar—H-2), 6.46-6.44 (dd, 1H, $^2J$=8.4 Hz, $^3J$=2.4 Hz, Ar—H8), 6.3 (d, 1H, J=2.4 Hz, ArH-4), 6.26 (d, 1H, J=2.4 Hz, ArH-10), 5.26 (s, 1H, 11a-H), 5.01 (s, 1H, 6a-OH), 4.14 (d, 1H, J=12 Hz H6 eq), 4.02 (d, 1H, J=12 Hz, H6 ax), 0.96 {s, 9H, Si(CH$_3$)$_3$}, 0.19 {s, 6H, Si(CH$_3$)$_2$}.

(+) 9-(t-Butyldimethylsilyloxy)-glycinol

Pinkish-white solid: 0.023 g (60%); mp 198-201° C.; TLC R$_f$0.38 in hexanes:EtOAc (2:1); $^1$H NMR (400 MHz, acetone-d$_6$) δ 8.55 (s. 1H, —OH), 7.31-7.29 (d, 1H, J=8.4 Hz, Ar—H1), 7.26-7.25 (d, 1H, J=8.4, Ar—H7), 6.56-6.54 (dd, 1H, $^2J$=8.4 Hz, $^3J$=2.4 Hz, Ar—H-2), 6.46-6.44 (dd, 1H, $^2J$=8.4 Hz, $^3J$=2.4 Hz, Ar—H8), 6.3 (d, 1H, J=2.4 Hz, ArH-4), 6.26 (d, 1H, J=2.4 Hz, ArH-10), 5.26 (s, 1H, 11a-H), 5.01 (s, 1H, 6a-OH), 4.14 (d, 1H, J=12 Hz, H6 eq), 4.02 (d, 1H, J=12 Hz, H6 ax), 0.96 {s, 9H, Si(CH$_3$)$_3$}, 0.19 {s, 6H, Si(CH$_3$)$_2$}.

EXAMPLE 5

Closure of the isoprenyl-containing ring within glyceollin-related compounds as exemplified by the specific method depicted in Scheme 5 (Step d).

General Procedure

To a solution of 9-(t-butyldimethylsilyloxy)glycinol (0.040 g, 0.1 mmol) in 5 mL of xylene was added 1,1-diethoxy-3-methyl-2-butene (0.2 mmol in 0.2 mL of xylene) and 3-picoline (0.025 mmol in 0.3 mL xylene). The reaction mixture was refluxed at 130° C. for 18 hours. After disappearance of reactant (TLC), the solvent was evaporated and the residue was chromatographed over silica using DCM as eluant. The organic fractions were evaporated to provide two yellowish oils: a major isomer I and a minor isomer II in ca. 5:1 ratio.

(+) 9-(t-Butyldimethylsilyloxy)-glyceollin I

Major yellow oil: 0.022 g (50%); TLC R$_f$0.46 in toluene:methanol (10:1); $^1$H NMR (400 MHz, acetone-d$_6$) δ 7.28-7.27 (d, 1H, J=8.4 Hz, Ar—H1), 7.25-7.23 (d, 1H, J=8.4 Hz, Ar—H7), 6.57 (d, 1H, J=9.6 Hz, H12), 6.48-6.45 (m, 2H, Ar—H7/Ar—H8), 6.3 (d, 1H, Ar-10H), 5.65 (d, 1H, J=10.2 Hz, H13), 5.27 (s, 1H, 11a-H), 5.09 (s, 1H, 6a-OH), 4.21-4.19 (d, 1H, J=11.4 Hz, H6 eq), 4.09-4.07 (d, 1H, J=11.4 Hz, H6 ax), 1.38-1.35 (2 s, 2×3H, H15/H16), 0.96 {s, 9H, Si(CH$_3$)$_3$}, 0.19 {s, 6H, Si(CH$_3$)$_2$}; $^{13}$C NMR (100 MHz, acetone-d$_6$) δ 162.3, 159.3, 155.4, 152.2, 132.7, 130.7, 125.6, 124, 117.6, 114.7, 114.1, 111.7, 111.2, 103.9, 86.5, 77.3, 77.2, 71.5, 28.6, 26.6, 19.3; HRMS Calc. [M$^+$+Na] 475.1917. found 475.1923.

(+) 9-(t-Butyldimethylsilyloxy)-glyceollin II

The other yellowish oil obtained in smaller amount from the above reaction: 0.0045 g (10%); TLC R$_f$0.40 in Toluene: Methanol (10:1); $^1$H NMR (400 MHz, acetone-d$_6$) δ 7.27-7.25 (d, 1H, J=7.8 Hz, Ar—H7), 7.14 (s, 1H, Ar—H1), 6.46-6.45 (dd, 1H, $^2J$=8.4 Hz, $^3J$=2.4 Hz, Ar—H8), 6.41-6.39 (d, 1H, J=9.6 Hz, Ar—H12), 6.27 (d, 1H, J=1.8 Hz, 11H), 6.21 (s, 1H, Ar—H4), 5.65 (d, 1H, J=10.2 Hz, Ar—H13), 5.25 (s, 1H, 11a-H), 5.07 (s. 1H, 6a-OH), 4.15-4.13 (d, 1H, J=11.1 Hz, H6 eq), 4.03-4.01 (d, 1H, J=11.4 Hz, H6 ax), 1.38-1.35 (2 s, 2×3H, H15/H16), 0.96 {s, 9H, Si(CH$_3$)$_3$}, 0.19 {s, 6H, Si(CH$_3$)$_2$}. $^{13}$C NMR (100 MHz, acetone-d$_6$) δ 162.3, 159.4, 157.9, 130.6, 130.4, 125.7, 124.1, 122.8, 117.8, 114.8, 114.1, 105.4, 103.9, 86.3, 77.8, 77.3, 71.2, 28.9, 26.6, 19.3; HRMS Calc. [M$^+$+Na] 475.1917. found 475.1919.

9-(t-Butyldimethylsilyloxy)-glyceollin I

Major yellow oil: 0.027 g (61%); TLC R$_f$0.46 in toluene:methanol (10:1); $^1$H NMR (400 MHz, acetone-d$_6$) δ 7.28-7.27 (d, 1H, J=8.4 Hz, Ar—H1), 7.25-7.23 (d, 1H, J=8.4 Hz, Ar—H7), 6.57 (d, 1H, J=9.6 Hz, H12), 6.48-6.45 (m, 2H, Ar—H7/Ar—H8), 6.3 (d, 1H, Ar-10H), 5.65 (d, 1H, J=10.2 Hz, H13), 5.27 (s, 1H, 11a-H), 5.09 (s, 1H, 6a-OH), 4.21-4.19 (d, 1H, J=11.4 Hz, H6 eq), 4.09-4.07 (d, 1H, J=11.4 Hz, H6 ax), 1.38-1.35 (2×s, 2×3H, H15/H16), 0.96 {s, 9H, Si(CH$_3$)$_3$}, 0.19 {s, 6H, Si(CH$_3$)$_2$}.

(+) 9-(t-Butyldimethylsilyloxy)-glyceollin I

Major yellow oil: 0.025 g (57%); TLC R$_f$ 0.46 in toluene: methanol (10:1); $^1$H NMR (400 MHz, acetone-d$_6$) δ 7.28-7.27 (d, 1H, J=8.4 Hz, Ar—H1), 7.25-7.23 (d, 1H, J=8.4 Hz, Ar—H7), 6.57 (d, 1H, J=9.6 Hz, H12), 6.48-6.45 (m, 2H, Ar—H7/Ar—H8), 6.3 (d, 1H, Ar-10H), 5.65 (d, 1H, J=10.2 Hz, H13), 5.27 (s, 1H, 11a-H), 5.09 (s, 1H, 6a-OH), 4.21-4.19 (d, 1H, J=11.4 Hz, H6 eq), 4.09-4.07 (d, 1H, J=11.4 Hz, H6 ax), 1.38-1.35 (2 s, 2×3H, H15/H16), 0.96 {s, 9H, Si(CH$_3$)$_3$}, 0.19 {s, 6H, Si(CH$_3$)$_2$}.

EXAMPLE 6

Removal of the TBDMS protecting group applicable to various glyceollin-related compounds as exemplified by the uniquely specific method shown in Scheme 5 (Step e).
General Procedure
9-(t-Butyldimethylsilyloxy)-glyceollin I (0.043 g, 0.1 mmol) was dissolved in 1 mL of acetonitrile and the solution was cooled to −20° C. N(Et)$_3$.3HF in acetonitrile (1.2 mL, 0.12 mmol) was added and the mixture stirred for 8 hours at 4° C. After disappearance of reactant (TLC), the pH was adjusted to 7-8 by addition of triethylamine and the mixture filtered through a silica column using DCM:MeOH (100:10). Evaporation of the solvent at 20° C. provided a brownish oily residue which was chromatographed over silica using hexanes:DCM:methanol (10:10:1). The organic fractions were evaporated at 20° C. to provide the solids specified below.

(+) Glyceollin I (Racemic Glyceollin I)

White solid with red tinge: 0.023 g (69%); TLC R$_f$ 0.22 in hexanes:DCM:methanol (10:10:1); Chiral HPLC showed two peaks of ca. equal area; $^1$H NMR (400 MHz, methanol-d$_4$) δ 7.21-7.19 (d, 1H, J=8.4 Hz, Ar—H1), 7.07 (d, 1H, J=8.4 Hz, Ar—H7), 6.51-6.49 (d, 1H, J=10.2 Hz, H12), 6.38-6.36 (d, 1H, J=8.4 Hz, Ar—H7), 6.31-6.29 (dd, 1H, $^2$J=8.4 Hz, $^3$J=2.4 Hz, Ar—H8), 6.13 (d, 1H, J=2.4 Hz, Ar—H7), 5.53-5.51 (d, 1H, J=10.2 Hz, H13), 5.06 (s, 1H, 11a-H), 4.81 (s, 1H, 6a-OH), 4.08-4.06 (d, 1H, J=11.4 Hz, H6 eq), 3.94-3.92 (d, 1H, J=11.4 Hz, H6 ax), 1.38-1.35 (2 s, 2×3H, H15/H16); $^{13}$C NMR (100 MHz, Methanol d$_4$) δ 162.3, 161.3, 155.4, 151.9, 132.4, 130.5, 125.3, 121.3, 117.7, 114.3, 111.7, 111.4, 109.5, 99.1, 86.1, 77.3, 77.2, 71.3, 28.2; HRMS Calc. [M$^+$+Na] 361.1052. found: 361.1052.

Glyceollin I (Natural Glyceollin I)

White solid with red tinge: 0.026 g (77%); TLC R$_f$ 0.22 in hexanes:DCM:methanol (10:10:1); Chiral HPLC showed an essentially one peak chromatogram. $^1$H NMR (400 MHz, methanol-d$_4$) δ 7.21-7.19 (d, 1H, J=8.4 Hz, Ar—H1), 7.07 (d, 1H, J=8.4 Hz, Ar—H7), 6.51-6.49 (d, 1H, J=10.2 Hz, H12), 6.38-6.36 (d. 1H, J=8.4 Hz, Ar—H7), 6.31-6.29 (dd, 1H, $^2$J=8.4 Hz, $^3$J=2.4 Hz, Ar—H8), 6.13 (d, 1H, J=2.4 Hz, Ar—H7), 5.53-5.51 (d, 1H, J=10.2 Hz, H13), 5.06 (s, 1H, 11a-H), 4.81 (s, 1H, 6a-OH), 4.08-4.06 (d, 1H, J=11.4 Hz, H6 eq), 3.94-3.92 (d, 1H, J=11.4 Hz, H 6ax), 1.38-1.35 (2 s, 2×3H, H15/H16); HRMS Calc. [M$^+$+Na] 361.1052. found: 361.1059.

(+) Glyceollin I (Unnatural Glyceollin I)

White solid with yellow tinge: 0.025 g (75%); TLC R$_f$ 0.22 in hexanes:DCM:methanol (10:10:1); Chiral HPLC showed an essentially one peak chromatogram; $^1$H NMR (400 MHz, methanol-d$_4$) δ 7.21-7.19 (d, 1H, J=8.4 Hz, Ar—H1), 7.07 (d, 1H, J=8.4 Hz, Ar—H7), 6.51-6.49 (d, 1H, J=10.2 Hz, H12), 6.38-6.36 (d. 1H, J=8.4 Hz, Ar—H7), 6.31-6.29 (dd, 1H, $^2$J=8.4 Hz, $^3$J=2.4 Hz, Ar—H8), 6.13 (d, 1H, J=2.4 Hz, Ar—H7), 5.53-5.51 (d, 1H, J=10.2 Hz, H13), 5.06 (s, 1H, 11a-H), 4.81 (s, 1H, 6a-OH), 4.08-4.06 (d, 1H, J=11.4 Hz, H6 eq), 3.94-3.92 (d, 1H, J=11.4 Hz, H6 ax), 1.38-1.35 (2 s, 2×3H, H15/H16); HRMS Calc. [M$^+$+Na] 361.1052. found: 361.1059.

(+) Glyceollin II (Racemic Glyceollin II)

White solid: 0.004 g (65%); TLC, R$_f$ 0.20 in hexanes:DCM: methanol (10:10:1); NMR (600 MHz, methanol-d$_4$) δ 7.15-7.14 (d, 1H, J=8.4 Hz, Ar—H7), 7.09 (s, 1H, Ar—H1), 6.39-6.38 (dd, 1H, $^2$J=8.4 Hz, $^3$J=2.4 Hz, Ar—H8), 6.37-6.35 (d, 1H, J=9.6 Hz, H12), 6.24 (s, 1H, Ar—H4), 6.22-6.21 (d, 1H, J=1.8 Hz, Ar—H10), 5.62-5.6 (d, 1H, J=10.2 Hz, H13), 5.15 (s, 1H, 11a-H), 4.11-4.10 (d, 1H, J=11.4 Hz, H6 eq), 3.91-3.88 (d, 1H, J=11.4 Hz, H6 ax), 1.38-1.35 (2 s, 2×3H, H15/H16). $^{13}$C NMR (100 MHz, Methanol-d$_4$) δ 162.3, 161.4, 157.3, 155.9, 130.4, 130, 125.3, 122.8, 117.9, 114.5, 109.5, 105.4, 99.1, 90.8, 85.9, 77.8, 77.3, 71.1, 28.5, 28.4, HRMS Calc. [M$^+$+Na] 361.1052. found: 361.1045.

(+) Glycinol 9-(t-Butyldimethylsilyloxy)-glycinol I (0.039 g, 0.1 mmol) was dissolved in 1 mL of acetonitrile and the solution was cooled to −20° C. N(Et)$_3$.3HF in acetonitrile (1.2 mL, 0.12 mmol) was added and the mixture stirred for 12 hours at 4° C. After disappearance of reactant (TLC), the pH was adjusted to 7-8 by addition of triethylamine and the mixture filtered through a silica column using DCM:MeOH (100:10). Evaporation of the solvent at 20° C. provided a brownish oily residue which was chromatographed over silica using hexanes:DCM:methanol (10:10:1). The organic fractions were evaporated at 20° C. to provide an orange solid: (0.018 g, 66%); TLC, R$_f$ 0.25 in DCM:methanol (10:1); $^1$H NMR (400M Hz, methanol-d$_4$) δ 8.51 (s, 1H, OH), 7.3 (d, 1H, J=9.0 Hz, Ar—H1), 7.20-7.18 (d, 1H, J=8.4 Hz, Ar—H7), 6.55-6.53 (dd, 1H, $^2$J=8.4 Hz, $^3$J=2.4 Hz, Ar—H2), 6.42-6.40 (dd, 1H, $^2$J=8.4 Hz, $^3$J=2.4 Hz, Ar—H8), 6.30 (d, 1H, J=2.4 Hz, Ar—H4), 6.23 (d, 1H, J=1.8 Hz, Ar—H10), 5.25 (s, 1H, 11aH), 4.91 (s, 1H, 6a-OH), 4.11-4.09 (d, 1H, J=11.4 Hz, H6 eq), 4.02-4 (d, 1H, J=11.4 Hz, H6 ax). $^{13}$C NMR (100 MHz, acetone-d$_6$) δ 161.3, 160.0, 158.9, 156.4, 132.6, 124.5, 120.8, 112.7, 110, 108, 103.1, 97.9, 85.3, 76.1, 69.9; analysis calcd. for C$_{15}$H$_{12}$O$_5$. 1.0C$_2$H$_6$O. 0.05H$_2$O C, 65.28; H, 5.51; O, 29.23. found: C, 64.88; H, 5.33; O, 29.23. HRMS Calc. [M$^+$+Na] 295.0582. found: 295.0571.

EXAMPLE 7

This example illustrates how the biological data pertaining to antioxidant properties of the compounds was obtained.
ABTS Assay Method
The antioxidant activity of each test agent was assayed by a colorimetric assay described in the literature that utilizes 2,2'-azinobis-3-ethylbenzothiazoline-6-sulfonic acid (ABTS). ABTS has an intense blue-green color in its free radical form, but is colorless without the free radical. Free radical ABTS was generated by reacting 7 mM ABTS with 2.45 mM potassium persulfate in water for 24-48 hr at room temperature in the dark. Test agents were diluted in 50/50 phosphate buffered saline (PBS)/ethanol to a series of five concentrations, then added to a 96 well half-area plate using 50 µl per well with four wells for each agent concentration. Four control wells containing 50/50 PBS/ethanol without test agents were setup for comparison for each test agent. Trolox, a water-soluble form of vitamin E commonly employed as an antioxidant standard, was also tested in each set of experiments. The free radical ABTS solution was diluted with 50/50 PBS/ethanol to give an absorbance of 1.4 absorbance units at 734 nm, and was then added 50 µl per well to two of the four wells for each condition. The other two wells for each condition received 50 µl of 50/50 PBS/ethanol without ABTS to provide background correction absorbance readings. All dilution and plate loading operations were performed on a Packard Multiprobe II HTS automated liquid handling system. Plates were kept in the dark for two minutes at room temperature, after which the absorbance of each well was measured at 732 nm on a Molecular Devices M5 plate reader. Readings for wells with ABTS were background corrected using the corresponding wells containing matching test agent levels without ABTS. The background corrected absorbance of each test agent concentration was then compared to the control wells without agent to determine the percent decrease in color intensity, corresponding to the percent of ABTS free radical reduction. A fit of percent absorbance decrease versus test agent concentration was then used to estimate the concentration causing a 50% reduction in absorbance, called the $IC_{50}$. The test agent $IC_{50}$ values were then compared to the $IC_{50}$ of trolox to calculate the trolox equivalents (TE, moles of trolox needed to give the same level of antioxidant activity as one mole of test agent) for each agent. Smaller $IC_{50}$ values or larger TE values indicate higher levels of antioxidant activity.

EXAMPLE 8

This example illustrates how the biological data pertaining to interaction of the compounds with the alpha-estrogen receptors was obtained.
ER-α Binding Assays
A 200 µM working stock solution of GLY I was prepared from an original 10 mM DMSO stock solution. The working stock solution was serially diluted in triplicate in screening buffer to the desired concentrations. hrER-α and ES2 were added to a final concentration of 2 nM and 3 nM, respectively. Negative (ER+ES2, equivalent to 0% inhibition) and positive (free ES2, equivalent to 100% inhibition) controls in the absence of competitor were measured in duplicate. After 2 h at room temperature, the anisotropy values in each tube were measured using the Beacon 2000 system CO. The anisotropy values were converted to percent inhibition using the following formula: $I_\% = (A_0 - A)/(A_0 - A_{100}) \times 100$, where $I_\%$ is the percent inhibition, $A_0$ is 0% inhibition, $A_{100}$ is 100% inhibition, and A represents the observed value. Polarization values were converted to percent inhibition to make the data more intuitive to the reader and to normalize the day-to-day differences in the starting 0% inhibition polarization values. The percent inhibition versus competitor concentration curves were analyzed by nonlinear least-squares curve fitting and yielded an $IC_{50}$ value (the concentration of competitor needed to displace half of the bound ligand). To compare binding affinities of the test compounds to those reported in the literature, $IC_{50}$ values were converted to relative binding affinities (RBA) using $E_2$ as a standard. The $E_2$ RBA was set equal to 100 [RBA=($IC_{50}/IC_{50}$ of $E_2$)×100].

EXAMPLE 9

This example illustrates how the in vitro biological data pertaining to estrogenic effects, anticancer and cancer preventative properties of the compounds was obtained.
Cell Culture Studies (MCF7 ER-Positive Cells)
Human cancer cell lines derived from breast (MCF7, ER-positive cells) were cultured in 75 ml culture flasks in DMEM (Invitrogen, Co.) supplemented with 10% FBS (Life Technologies, Inc., Gaithersburg, Md.), basic minimum MEM essential (50×, Invitrogen Co.) and MEM non-essential (100×, Invitrogen, Co.) amino acids, sodium pyruvate (100× Invitrogen Co.), antimicotic-antibiotic (10,000 U/mL penicillin G sodium; 10,000 µg/mL streptomycin sulphate; 25 µg/mL amphotericin B as Fungizone®), and human recombinant insulin (4 mg/mL. Invitrogen Co.). The culture flasks were maintained in a tissue culture incubator in a humidified atmosphere of 5% $CO_2$ and 95% air at 37° C. For estrogen studies, cells were washed with PBS 3 times and grown in phenol red-free DMEM supplemented with 5% dextran-coated charcoal-treated FBS (5% CS-FBS) for 72 h before plating for each particular experiment.
Results were then assessed by using an ERE-luciferase assay. The cells were plated in 24 well plates at 5×10⁵ cells/well in the same media and allowed to attach overnight. After 18 hours, cells were transfected for 5 h in serum supplemented-free DMEM with 300 µg pGL2-ERE2X-TK-luciferase plasmid, using 6 µl of effectine (Qiagen)/µg of DNA. After 5 h the transfection medium was removed and replaced with phenol red-free DMEM supplemented with 5% CS-FBS containing vehicle, 17β-estradiol, GLY I, or 17β-estradiol plus GLY I, and incubated at 37° C. After 18 h the medium was removed, and 100 µl of lysis buffer was added per well and then incubated for 15 min at room temperature. Cell debris was pelleted by centrifugation at 15000×g for 5 min. cell extracts were normalized for protein concentration using reagent according to the protocol supplied by the manufacturer (Bio-Rad Laboratories, Inc., Hercules, Calif.). Luciferase activity for the cell extracts was determined using Luciferase substrate (Promega Corp.) in an Autoluminat Plus luminometer.
Cell Culture Studies (MCF7 Non-Estrogen Responsive; MCF12A; and NCI/ADR-RES) Growth Inhibition Assay Method
Test agent inhibition of cell growth was assayed by the method employed in the U.S. National Cancer Institute (NCI) in vitro anticancer screening program. MCF7 and NCI/ADR-RES cells (NCI) were maintained in RPMI 1640 media containing 2 mM L-glutamine supplemented with 2 mg/ml sodium bicarbonate, 25 mM HEPES, 5% fetal bovine serum (FBS), 5% NuSerum IV, and 50 µg/ml gentamicin. MCF12A cells (ATCC) were cultured in a 1:1 mixture of DMEM and F-12 Ham media containing 2.5 mM L-glutamine supplemented with 2 mg/ml sodium bicarbonate, 15 mM HEPES, 10 mg/L insulin, 500 µg/L hydrocortisone, 20 µg/L Epidermal Growth Factor, 100 µg/L cholera toxin, and 5% FBS. Cells were passaged weekly and incubated at 37° C. in a humidified 95% air/5% $CO_2$ atmosphere. Cells were removed from the culture flasks by trypsinization, counted on a hemocytometer, and then loaded into 96 well plates via 100 µl media per well at cell densities of 1800 cells per well (cpw) for MCF7, 3300 cpw for NCI/ADR-RES, and 1100 cpw for MCF12A. After overnight culture to allow the cells to attach, test agents were added via a 100 µl media addition at five 10-fold serially diluted concentrations. Control wells received matching levels of DMSO agent vehicle (final level 0.25% DMSO). Plates were cultured 48 hr with test agents, after which they were fixed with 50 µl per well of chilled 50% trichloroacetic acid. Fixed plates were refrigerated for 1-2 hr, then rinsed five times with chilled deionized water and allowed to dry. Plates were then stained with 50 µl per well of aqueous solution containing 0.4% sulforhodamine B and 1% acetic acid in deionized water, rinsed five times with 1% acetic acid in deionized water, and again allowed to dry. Finally, the bound dye was resuspended with 150 µl per well of 10 mM Tris-Base (pH 10.5), and the optical density of each well was measured at 565 nm on a Molecular Devices M5 plate reader. One plate was fixed immediately after agent addition and then stained along with the other plates to provide a reading of the optical density at the start of the agent exposure period. The difference between the optical density at the beginning and end of the agent exposure period provided a measure of the cell growth, and the ratio for a given agent level versus control wells offered a measure of the fraction of control cell growth. The test agent concentration that caused a 50% reduction in cell growth versus the control wells, called the $GI_{50}$, was estimated for each agent with each cell line from a Hill Equation fit of the fraction of control growth versus agent concentration. A smaller $GI_{50}$ value indicates higher growth inhibition activity.

EXAMPLE 10

This example provides a prophetic illustration of how in vivo biological data pertaining to the estrogenic, anticancer and cancer preventative properties of the compounds would be obtained.

Cells and Reagents

The MCF-7N cell variant is a subclone of MCF-7 cells from the American Type Culture Collection (Manassas, Va.) and has been previously described in the literature. MCF-7 cells are grown in Dulbecco's modified minimal medium (pH 7.4; Life Technologies, Inc., Grand Island, N.Y.) supplemented with 10% fetal bovine serum (Hyclone, Salt Lake City, Utah). Cells are incubated at 37° C. in an atmosphere of 5% $CO_2$ and air.

Animals

NU/NU immune-compromised female ovariectomized mice (29-32 days old) are obtained from Charles River Laboratories (Wilmington, Mass.). The animals are allowed a period of adaptation in a sterile and pathogen-free environment with phytoestrogen-free food and water ad libitum. Mice are divided into 4 treatment groups of five mice each: Control (con), Estradiol only (E2), Drug only (e.g. GLY I only), and Estradiol plus Drug (e.g. E2+GLY I). Placebo or estradiol pellets (0.72 mg, 60-day release, Innovative Research of America) are implanted subcutaneously in the lateral area of the neck in the middle point between the ear and shoulder using a precision trochar (10 gauge). MCF-7 and BG-1 cells in the exponential phase of growth are harvested using PBS/EDTA solution and washed. Viable cells ($5 \times 10^6$) in a 50 µl sterile PBS suspension are mixed with 100 µl Matrigel Reduced Factors (BD Biosciences, Bedford, Mass.). MCF-7 cells are injected on the right side of the mammary fat pad (MFP) through a 5 mm incision at the hypogastrium area, and the incision is closed using staples. All the procedures in animals are carried out under anesthesia using a mix of isofluorane and oxygen, delivered by mask.

Drug (e.g. GLY I) is suspended in a solution of DMSO (⅓ volume) and propylene glycol (⅔ volume) and is administered subcutaneously in the dorsal area at 20 mg/kg/mouse/day for 20 days to Drug, and E2+Drug groups starting on the same day of tumor implantation (Day 1). Con and E2 groups are injected with vehicle daily for 20 days. Tumor size is measured every two days using a digital caliper. The volume of the tumor is calculated using the following formula: $4/3\pi LM_2$, where L is the larger diameter and M is the smaller diameter. At necropsy on day 21, animals are euthanized by decapitation after exposure to a $CO_2$ chamber. Tumors, uteri, brain, livers, and lungs are removed and either frozen in liquid nitrogen or fixed in 10% formalin for further analysis.

Immunohistochemistry Assay

Tumor explants are collected at necropsy, fixed in 70% ethanol, embedded in paraffin, and immunostained using a primary monoclonal antibody for human progesterone receptor (PR) (NCL-PGR, Novocastra, Newcastle-upon-Tyne, UK). Expression of PR is upregulated through ER-mediated pathways and thus serves as a marker of estrogen exposure within target tissues. Staining methods include antigen-retrieval with citrate buffer (pH 6.0), biotinylated rabbit anti-mouse Fc antibody as a linking reagent, alkaline phosphatase-conjugated streptavidin as the label, and Vector Red as the chromogen (Vector Laboratories, Burlingame, Calif.). Cell staining is quantified by a computer-assisted counting technique, using a grid filter to select cells for counting. At least two microscopic fields are randomly selected for each tumor, and 200 cells are counted at 20× magnification. Numbers of positively stained cells are expressed as a percentage of the total number examined. All measurements are made blinded to treatment group.

Assessment of Uterine Morphology

Uteri are removed at necropsy, weighed, fixed in 10% formalin for 24 hrs, transferred to 70% ethanol, sectioned transversely through each uterine horn, embedded in paraffin, and stained with hematoxylin and eosin by routine procedures. Slides are photographed at 2× and 40× magnification using a Nikon CoolPix E995 digital camera (Melville, N.Y.). Uterine area, thickness, and epithelial height are measured from digital images using public domain software (NIH Image v1.62; available at http://rsb.info.nih.gov/nih-image/download.html). For epithelial height, three separate measurements are taken, and the average is used for each animal. H&E-stained uteri are also evaluated qualitatively for histological changes.

Statistics

Data for MCF-7-N tumor size are analyzed separately using repeated measures two-way ANOVA with treatment and time as independent factors (SigmaStat 3.1). Data may fail normality testing and if so are rank-transformed before analysis. Power for each of these comparisons (treatment, trial day, treatment×trial day) is 1.0. Post-hoc multiple pairwise comparisons testing using the Holm-Sidak method, which makes adjustments for the number of comparisons, follows. Data for PR expression and uterine morphology are subjected to one-way analysis of variance. Variables are evaluated for their distribution and equality of variances between groups. Overall statistical significance levels are set at $p<0.05$, but critical p levels for individual pairwise comparisons are adjusted for the number of comparisons. All data are reported as treatment group means±SEM.

EXAMPLE 11

It should be apparent to a practitioner having routine knowledge of the common art, that the pure forms of the substances disclosed herein can be used according to standard practices for the formulation of various therapeutic products, as well as for deployment as additives to various types of enhanced or medicinal food products, dietary supplements and nutraceuticals. Alternatively, it is less apparent that the overall inventive process now allows for any combination of these pure substances to be remixed into various composites according to predetermined ratios, said composites then also being useful for the formulation of various therapeutic products, and as additives to various types of enhanced or medicinal food products, dietary supplements and nutraceuticals. Particularly valuable and useful in this regard is that the quality control afforded by mixing pure materials to achieve specified ratios of the components, is excellent compared to that associated with the production of such materials starting from natural sources because the nuances of natural growth within even well-controlled environments will not lead to the same precision in the various component ratios. Illustrating how readily the mixing of pure materials can now be practiced as a result of the inventors' inventions, while not intending to be inclusive of either the selected substances, their component ratios or the scale of operation, the following Table 3 exemplifies how predetermined ratios of GLY I and GLY II can be achieved within a composite of a single solid admixture at the 100 gram scale. Solution composites can likewise be achieved by either dissolving the solid admixture into a desired solvent, by dissolving the specified weight of each component into the desired solvent and then combining the two solvents in equal portions, or by using various concentrations of pure component solutions that are then combined according to standard practices determined by routine solution molarity calculations.

TABLE 3

Mixing Pure GLY I With Pure GLY II To Obtained Predetermined Composites

| GLY I:GLY II Ratio | GLY I (g) | GLY II (g) |
|---|---|---|
| 5 to 1 | 83.4 | 16.6 |
| 4 to 1 | 80.0 | 20.0 |
| 3 to 1 | 75.0 | 25.0 |
| 2 to 1 | 66.7 | 33.3 |
| 1 to 1 | 50.0 | 50.0 |
| 1 to 2 | 33.3 | 66.7 |
| 1 to 3 | 25.0 | 75.0 |
| 1 to 4 | 20.0 | 80.0 |
| 1 to 5 | 16.0 | 83.0 |

EXAMPLE 12

Soybean plant parts can be stressed and elicited so as to produce various mixtures of the glyceollin-related materials in various ranges for which the latter become subject to the various conditions of growth, the various conditions of stress, and finally the various conditions of their processing upon harvest. In the penultimate step of the overall synthetic process disclosed herein, GLY I and GLY II (still protected as their TBDMS ethers) are produced in a ratio of about 5 to 1 which, on a molar basis, is similar to the first entry in TABLE 3. While this ratio is also subject to the specific methodology and reaction conditions deployed to form the isoprenyl-ring system, such conditions are able to be controlled very closely within a laboratory setting compared to the more natural settings that soybean plant parts become subject to. Thus, the utility of the inventive method for directly producing various GLY I to GLY II mixtures wherein GLY I will always remain as the major component, from a synthetic process is illustrated by the specific example provided below wherein a ca. 5 to 1 ratio is achieved. These types of synthetic procedures eliminate altogether the need for the chromatographic separation of GLY I from GLY II at this distinct step of the overall synthetic process when directed towards producing pure single materials. Because of this greater ease of production, this aspect of the overall inventive method becomes additionally practical for the preparation of these particular types of specific composite products.

Racemic GLY I Plus GLY II Composite Product Having A 5 to 1 Ratio

The mixture of 9-(t-Butyldimethylsilyloxy)-glyceollin I and 9-(t-Butyldimethylsilyloxy)-glyceollin II (0.044 g, 0.1 mmol) was dissolved in 1 mL of acetonitrile and the solution was cooled to −20° C. N(Et)$_3$.3HF in acetonitrile (1.2 mL, 0.12 mmol) was added and the mixture stirred for 8 hours at 4° C. After disappearance of reactant (TLC), the pH was adjusted to 7-8 by addition of triethylamine and the mixture filtered through a silica column using DCM:MeOH (100 10). Evaporation of the solvent at 20° C. provided a brownish oily residue which was chromatographed over silica using hexanes:DCM:methanol (10:10:1). The organic fractions were evaporated at 20° C. to provide a yellowish white solid having both components: 0.027 g (76%); TLC R$_f$ 0.22 and 0.20, hexanes:DCM:methanol (10:10:1).

In accordance with the provisions of the patent statutes, the principle modes of operation of this invention have been explained and illustrated and the preferred embodiments have been disclosed. It is to be understood that this invention may be practiced otherwise than as specifically explained and illustrated without departing from its spirit or scope. In particular is a degree of flexibility within the synthetic methods to be used wherein different types of chemical protecting groups might also be deployed, providing that any of such other protecting groups also still meet the unique requirements disclosed within the 'general description of the broadest embodiments.' For example, the inventors' specific description of the t-butyldimethylsilyl-group (TBDMS) as a distinct species, should be taken to include the use of the several other similar types of silyl-protecting groups, namely triethylsilyl (TES), triisopropyl (TIPS), or t-butyldiphenylsilyl (TBDPS) Likewise, the inventors' specific description of the benzyl-group and of the acetyl-group as distinct species, should be taken to include the use of other aryl or aralkyl ethers, and of other simple ester forming alkyl and aryl carboxylic acid groups.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A method for treating breast or ovarian cancer, and/or for modulating estrogen receptors, comprising:

administering an effective amount of a composition comprising:
a) the compound

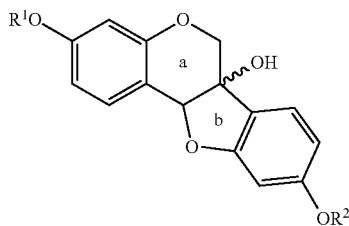

a pharmaceutically acceptable salt thereof made from an acid or a base, or a stereoisomer thereof; and
b) optionally, a further compound selected from the group consisting of:

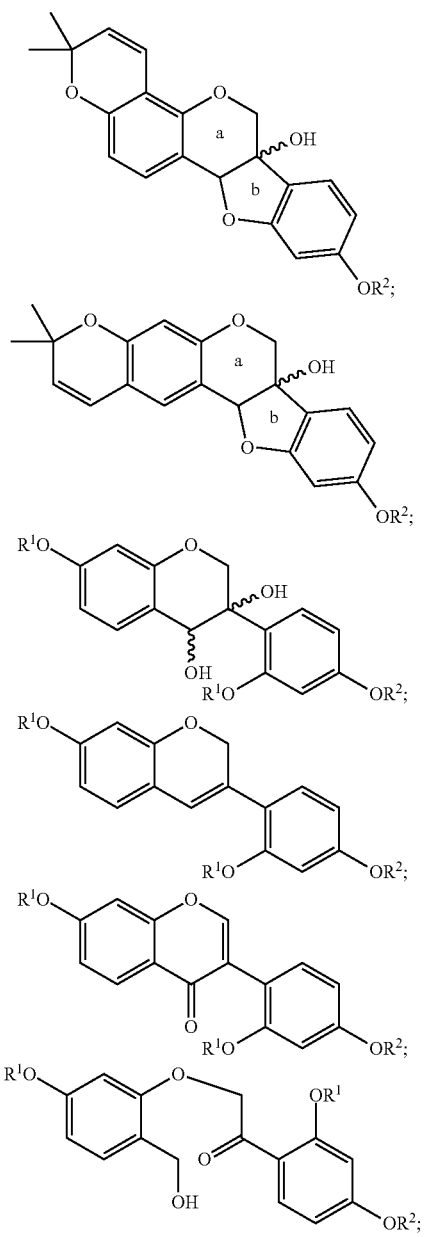

pharmaceutically acceptable salts thereof made from an acid or a base, or a stereoisomer thereof, and combinations thereof,
to a subject in need thereof, thereby treating said breast or ovarian cancer, and/or modulating said estrogen receptors
wherein:
the "a" to "b" ring systems are joined by a cis-fusion;
the 3,4-dihydroxy groups, when present, are in a cis-orientation;
$R^1$ is H, benzyl, or $Si[CH_3]_2[C(CH_3)_3]$; and
$R^2$ is H, benzyl, methoxymethyl, or $Si[CH_3]_2[C(CH_3)_3]$.

2. The method of claim 1, wherein said compound and said further compound are in substantially pure form.

3. The method of claim 2, wherein said pure form includes all stereoisomer possibilities.

4. The method of claim 1, wherein said compound and said further compound are formulated as an enhanced or medical food product, a dietary supplement product, or an ethical pharmaceutical product.

5. The method of claim 1, wherein said modulation of estrogen receptors comprises treatment of reduced bone mass, density, or strength, and/or treatment of menopausal and post-menopausal syndromes.

6. The method of claim 1, wherein said further compound is:

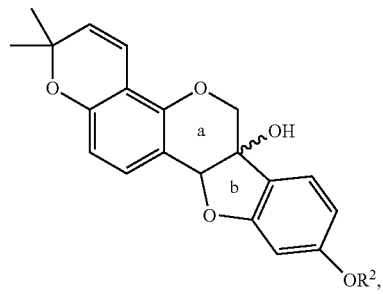

a pharmaceutically acceptable salt thereof made from an acid or a base, or a stereoisomer thereof.

7. The method of claim 1, wherein said further compound is:

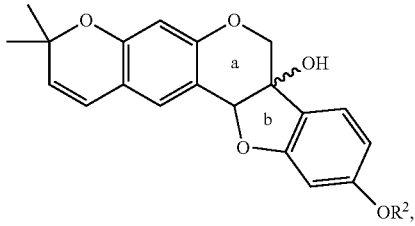

a pharmaceutically acceptable salt thereof made from an acid or a base, or a stereoisomer thereof.

8. The method of claim 1, wherein said method is for treating breast cancer.

9. The method of claim 1, wherein said method is for treating ovarian cancer.

10. The method of claim 1, wherein said method is for modulating estrogen receptors.

* * * * *